United States Patent
Baroni et al.

(10) Patent No.: US 9,511,041 B2
(45) Date of Patent: *Dec. 6, 2016

(54) ALKYLAMIDO COMPOUNDS AND USES THEREOF

(71) Applicant: Nogra Pharma Limited, Dublin (IE)

(72) Inventors: Sergio Baroni, Villa d'adda (IT); Salvatore Bellinvia, Pordenone (IT); Francesca Viti, Sesto San Giovanni (IT)

(73) Assignee: Nogra Pharma Limited, Dublin (IE)

( * ) Notice: Subject to any disclaimer, the term of this patent is extended or adjusted under 35 U.S.C. 154(b) by 0 days.

This patent is subject to a terminal disclaimer.

(21) Appl. No.: 14/255,255

(22) Filed: Apr. 17, 2014

(65) Prior Publication Data

US 2015/0051285 A1    Feb. 19, 2015

Related U.S. Application Data

(63) Continuation of application No. 13/201,786, filed as application No. PCT/EP2010/000935 on Feb. 16, 2010, now Pat. No. 8,754,127.

(60) Provisional application No. 61/179,062, filed on May 18, 2009, provisional application No. 61/287,461, filed on Dec. 17, 2009.

(30) Foreign Application Priority Data

Feb. 16, 2009 (EP) ..................... 09425056

(51) Int. Cl.

| C07C 235/38 | (2006.01) |
|---|---|
| A61K 31/196 | (2006.01) |
| A61K 8/42 | (2006.01) |
| A61Q 19/02 | (2006.01) |
| A61Q 19/06 | (2006.01) |
| A61Q 19/08 | (2006.01) |
| C07D 307/79 | (2006.01) |
| C07D 319/08 | (2006.01) |
| C07C 233/54 | (2006.01) |

(52) U.S. Cl.
CPC .............. *A61K 31/196* (2013.01); *A61K 8/42* (2013.01); *A61Q 19/02* (2013.01); *A61Q 19/06* (2013.01); *A61Q 19/08* (2013.01); *C07C 233/54* (2013.01); *C07C 235/38* (2013.01); *C07D 307/79* (2013.01); *C07D 319/08* (2013.01); *A61K 2800/78* (2013.01)

(58) Field of Classification Search
CPC .. A61K 31/196; A61K 8/42; A61K 2800/78; A61Q 19/02; A61Q 19/06; A61Q 19/08; C07C 233/54; C07C 235/38; C07D 307/79; C07D 319/08
See application file for complete search history.

(56) References Cited

U.S. PATENT DOCUMENTS

| 3,211,610 A | 10/1965 | Rogers |
|---|---|---|
| 3,444,232 A | 5/1969 | Bernstein |
| 4,036,951 A | 7/1977 | Halpern et al. |
| 4,348,223 A | 9/1982 | Grove |
| 4,404,215 A | 9/1983 | Vincent et al. |
| 4,429,152 A | 1/1984 | Gries et al. |
| 4,720,506 A | 1/1988 | Munakata et al. |
| 4,933,330 A | 6/1990 | Jorgensen et al. |
| 5,262,549 A | 11/1993 | Telfer et al. |
| 5,302,751 A | 4/1994 | Manimaran et al. |
| 5,519,014 A | 5/1996 | Borody |
| 5,594,015 A | 1/1997 | Kurtz et al. |
| 5,594,151 A | 1/1997 | Stolowitz |
| 6,114,382 A | 9/2000 | Moretti |
| 6,194,627 B1 | 2/2001 | Geissler et al. |
| 6,326,364 B1 | 12/2001 | Lin et al. |
| 6,403,656 B1 | 6/2002 | Rivier et al. |
| 6,583,128 B2 | 6/2003 | Ekwuribe et al. |
| 6,602,869 B1 | 8/2003 | Galey et al. |
| 6,844,003 B2 | 1/2005 | Galey et al. |
| 6,884,821 B1 | 4/2005 | Shinoda et al. |
| 6,903,082 B2 | 6/2005 | Ekwuribe et al. |
| 7,098,025 B1 | 8/2006 | Auwerx et al. |
| 7,176,204 B2 | 2/2007 | Miyachi et al. |
| 7,425,578 B2 | 9/2008 | Ekwuribe et al. |
| 7,429,676 B2 | 9/2008 | Woltering et al. |
| 7,749,980 B2 | 7/2010 | Plourde, Jr. et al. |
| 7,998,474 B2 | 8/2011 | Kelly |
| 8,030,520 B2 | 10/2011 | Sundermeier et al. |
| 8,138,357 B2 | 3/2012 | Naccari et al. |
| 8,153,693 B2 | 4/2012 | Baroni et al. |
| 8,153,841 B2 | 4/2012 | Naccari et al. |
| 8,450,506 B2 | 5/2013 | Naccari et al. |
| 8,501,806 B2 | 8/2013 | Baroni et al. |
| 8,710,100 B2 | 4/2014 | Naccari et al. |

(Continued)

FOREIGN PATENT DOCUMENTS

| EP | 0055689 A1 | 7/1982 |
|---|---|---|
| EP | 0102833 A1 | 3/1984 |

(Continued)

OTHER PUBLICATIONS

U.S. Appl. No. 14/314,738, filed Jun. 25, 2014.
U.S. Appl. No. 13/785,485, filed Mar. 5, 2013.
U.S. Appl. No. 14/377,362, filed Aug. 7, 2014.
U.S. Appl. No. 14/394,916, filed Oct. 16, 2014.
U.S. Appl. No. 14/202,386, filed Mar. 10, 2014.
U.S. Appl. No. 15/088,654, Methods for Preventing or Reducing Colon Carcinogenesis, filed Apr. 1, 2016, Pending.
U.S. Appl. No. 14/969,939, Methods of Treating Hair Related Conditions, filed Dec. 15, 2015, Pending.

(Continued)

*Primary Examiner* — Sarah Pihonak
*Assistant Examiner* — Jason A Deck
(74) *Attorney, Agent, or Firm* — Goodwin Procter LLP

(57) ABSTRACT

Disclosed herein are compounds that may be specific to PPAR and/or EGF receptors, and methods of making and using same.

8 Claims, 11 Drawing Sheets

(56) References Cited

U.S. PATENT DOCUMENTS

| | | |
|---|---|---|
| 8,754,127 B2 | 6/2014 | Baroni et al. |
| 8,796,334 B2 | 8/2014 | Baroni et al. |
| 9,133,099 B2 | 9/2015 | Naccari et al. |
| 9,345,680 B2 | 5/2016 | Naccari et al. |
| 2003/0113815 A1 | 6/2003 | Houseknecht et al. |
| 2003/0133875 A1 | 7/2003 | Kelly |
| 2003/0220374 A1 | 11/2003 | Needleman |
| 2003/0229083 A1 | 12/2003 | Debnath et al. |
| 2004/0034067 A1 | 2/2004 | MacPhee |
| 2004/0115127 A1 | 6/2004 | Wright et al. |
| 2004/0132110 A1 | 7/2004 | Desreumaux et al. |
| 2006/0159648 A1 | 7/2006 | Davis et al. |
| 2006/0177444 A1 | 8/2006 | Horizoe |
| 2006/0270635 A1 | 11/2006 | Wallace et al. |
| 2007/0086967 A1 | 4/2007 | MacDonald |
| 2007/0149804 A1 | 6/2007 | Woltering et al. |
| 2009/0048343 A1 | 2/2009 | Naccari et al. |
| 2009/0118357 A1 | 5/2009 | Naccari et al. |
| 2010/0305077 A1 | 12/2010 | Baroni et al. |
| 2011/0105748 A1 | 5/2011 | Bhuniya et al. |
| 2011/0152225 A1 | 6/2011 | Baroni et al. |
| 2011/0288058 A1 | 11/2011 | Baroni et al. |
| 2011/0288177 A1 | 11/2011 | Baroni et al. |
| 2012/0053244 A1 | 3/2012 | Baroni et al. |
| 2012/0053245 A1 | 3/2012 | Baroni et al. |
| 2012/0157417 A1 | 6/2012 | Baroni et al. |
| 2012/0316230 A1 | 12/2012 | Naccari et al. |
| 2013/0005813 A1 | 1/2013 | Naccari et al. |
| 2015/0045436 A1 | 2/2015 | Naccari et al. |
| 2015/0051285 A1 | 2/2015 | Baroni et al. |
| 2015/0087678 A1 | 3/2015 | Baroni et al. |
| 2015/0087708 A1 | 3/2015 | Baroni et al. |
| 2015/0148418 A1 | 5/2015 | Baroni et al. |
| 2015/0250749 A1 | 9/2015 | Giuliani et al. |
| 2015/0265514 A1 | 9/2015 | Giuliani et al. |
| 2015/0265562 A1 | 9/2015 | Naccari et al. |
| 2015/0265563 A1 | 9/2015 | Naccari et al. |

FOREIGN PATENT DOCUMENTS

| | | |
|---|---|---|
| EP | 0279096 A2 | 8/1988 |
| EP | 0291159 A2 | 11/1988 |
| EP | 0352826 A2 | 1/1990 |
| EP | 0623104 B1 | 8/1997 |
| EP | 0938459 B1 | 7/2002 |
| EP | 1285908 A1 | 2/2003 |
| EP | 1348698 A1 | 10/2003 |
| EP | 0554291 B1 | 12/2003 |
| EP | 1373906 A1 | 1/2004 |
| EP | 1389044 A1 | 2/2004 |
| EP | 1607103 A1 | 12/2005 |
| EP | 1274407 B1 | 3/2006 |
| EP | 1801093 B1 | 3/2009 |
| EP | 1448995 B1 | 1/2011 |
| EP | 2107047 B1 | 9/2011 |
| GB | 767788 A | 2/1957 |
| GB | 1359560 | 7/1974 |
| JP | 2003-516310 A | 5/2003 |
| JP | 3425441 B2 | 7/2003 |
| JP | 3435651 B2 | 8/2003 |
| JP | 2004-528329 A | 9/2004 |
| JP | 2005-510733 A | 4/2005 |
| JP | 2009-242399 A | 10/2009 |
| WO | WO-94/00135 A1 | 1/1994 |
| WO | WO-95/31194 A1 | 11/1995 |
| WO | WO-98/06387 A2 | 2/1998 |
| WO | WO-98/43081 A1 | 10/1998 |
| WO | WO-00/59866 A1 | 10/2000 |
| WO | WO-01/02388 A1 | 1/2001 |
| WO | WO-01/25181 A1 | 4/2001 |
| WO | WO-01/79153 A1 | 10/2001 |
| WO | WO-02/46161 A1 | 6/2002 |
| WO | WO-02/077651 A1 | 10/2002 |
| WO | WO-02/085123 A1 | 10/2002 |
| WO | WO-02/095393 A2 | 11/2002 |
| WO | WO-2004/073622 A2 | 9/2004 |
| WO | WO-2005/012280 A1 | 2/2005 |
| WO | WO-2005/072113 A2 | 8/2005 |
| WO | WO-2005/084658 A1 | 9/2005 |
| WO | WO-2006/072175 A1 | 7/2006 |
| WO | WO-2007/010514 A2 | 1/2007 |
| WO | WO-2007/010516 A2 | 1/2007 |
| WO | WO-2007/096148 A1 | 8/2007 |
| WO | WO-2008/104557 A1 | 9/2008 |
| WO | WO-2009/080828 A2 | 7/2009 |
| WO | WO-2010/063470 A2 | 6/2010 |
| WO | WO-2010/063472 A1 | 6/2010 |
| WO | WO-2010/091892 A2 | 8/2010 |
| WO | WO-2010/091894 A2 | 8/2010 |
| WO | WO-2013/117744 A9 | 8/2013 |
| WO | WO-2013/156413 A1 | 10/2013 |
| WO | WO-2013/178815 A1 | 12/2013 |
| WO | WO-2013/178816 A1 | 12/2013 |
| WO | WO-2014/041140 A1 | 3/2014 |
| WO | WO-2014/041141 A1 | 3/2014 |

OTHER PUBLICATIONS

Ameho CK et al., Prophylactic Effect of Dietary Glutamine Supplementation on Interleukin 8 and Tumor Necrosis Factor Alpha Production in Trinitrobenzene Sulphonic Acid Induced Colitis, Gut, Oct. 1997, 41(4):487-93.

International Preliminary Report on Patentability and Written Opinion for International Application No. PCT/EP2013/052617 dated Aug. 12, 2014 (5 pages).

International Preliminary Report on Patentability and Written Opinion for International Application No. PCT/EP2013/069062 dated Mar. 17, 2015 (7 pages).

International Preliminary Report on Patentability and Written Opinion for International Application No. PCT/EP2013/069063 dated Mar. 17, 2015 (7 pages).

International Preliminary Report on Patentability and Written Opinion of the International Searching Authority for PCT/EP2009/008631, issued Jun. 7, 2011(13 pages).

International Preliminary Report on Patentability and Written Opinion of the International Searching Authority for PCT/EP2009/008633, issed Jun. 7, 2011 (6 pages).

International Preliminary Report on Patentability and Written Opinion of the International Searching Authority for PCT/EP2010/000935, issued Aug. 16, 2011 (7 pages).

International Preliminary Report on Patentability and Written Opinion of the International Searching Authority for PCT/EP2010/000939, issued Aug. 16, 2011 (8 pages).

International Preliminary Report on Patentability for PCT/EP13/057729 issued on Oct. 21, 2014 (6 pages).

International Preliminary Report on Patentability for PCT/EP2008/052354, completed May 22, 2009 (20 pages).

International Preliminary Report on Patentability for PCT/EP2008/068265, completed Apr. 12, 2010 (11 pages).

Julien B et al., 'Antifibrogenic Role of the Cannabinoid Receptor CB2 in the Liver,' Gastroenterology, 2005, 128(3):742-55.

Kloepper et al., "Immunophenotyping of the human bulge region: the quest to define useful in situ markers for human epithelial hair follicle stem cells and their niche," Experimental Dermatology, vol. 17, pp. 592-609 (2008).

Pershadsingh et al., "Improvement in Psoriasis with Rosiglitazone in a Diabetic and a Nondiabetic Patient," Skinmed, vol. 4, pp. 386-390 (2005). (Abstract Only).

Speca, S. et al. (2012) "Cellular and Molecular Mechanisms of Intestinal Fibrosis," World Journal of Gastroenterology 18 (28), 3635-3661.

Wallace JL et al., 'Inhibition of Leukotriene Synthesis Markedly Accelerates Healing in Rat Model of Inflammatory Bowel Disease,' Gastroenterology, 1989, 96(1):29-36.

Written Opinion of the International Searching Authority for PCT/EP2008/052354 mailed Jun. 9, 2008 (10 pages).

Written Opinion of the International Searching Authority for PCT/EP2008/068265 mailed Aug. 11, 2009 (12 pages).

(56) References Cited

OTHER PUBLICATIONS

Wu X et al., 'Effects of Rosiglitazone on Expression of TGF-A1 in Experimental Hepatic Fibrosis Rats,' Chin J Gastroenterol Hepatol, 15(2):126-9 (2006).
Yu J et al., 'Peroxisome Proliferator-Activated Receptors Gamma Reverses Hepatic Nutritional Fibrosis in Mice and Suppresses Activation of Hepatic Stellate Cells in vitro,' Int J Biochem Cell Biol, Jun. 2010 Feb. 13, 2010 (ePub), 42(6):948-57.
Ahnfelt-Ronne et al. (1990) "Clinical Evidence Supporting the Radical Scavenger Mechanism of 5-Aminosalicylic Acid," Gastroenterology, 98:1162-1169.
Allgayer, H. (2003) "Review Article: Mechanisms of Action of Mesalazine in Preventing Colorectal Carcinoma in Inflammatory Bowel Disease," Aliment Pharmacol. Ther., 18 (Suppl. 2): 10-14.
Australian Examination Report dated Jan. 31, 2014, for Application No. 2009321722 (9 pages).
Baker et al., (1962) "Potential Anticancer Agents. LXXVIII Nonclassical Antimetabolites. IV. Synthesis of Compounds Related to 4-(Iodoacetamido) Salicylie Acid, an Exo-Alkylating Irreversible Inhibitor," Journal of Organic Chemistry, 27:3283-3295.
Baz, et al. (2003) "Oxidant / Antioxidant Status in Patients with Psoriasis," *Yonsei Medical Journal* 44:(6)987-990.
Behshad et al., "A Retrospective Case Series Review of the Peroxisome Proliferator-Activated Receptor Ligand Rosiglitazone in the Treatment of Atopic Dermatitis", Arch Dermatol, 144(1):8488 (2008).
Beilstein Database Beistein Institute zur Forderung der Chemischen Wissenschaften, Frankfurt an Main, DE XP002413839, Accession No. 2092096, J. Med. Chem., 22: 589 (1979).
Beilstein Database, Beilstein Institute for Organic Chemistry, Frankfurt an Main, DE, retrieved from XFIRE, Accession No. brn 2208094, J. Am. Chem. Soc., 68: 2335, 2338 (1946).
Beilstein Database, Beilstein Institute for Organic Chemistry, Frankfurt an Main, DE, retrieved from XFIRE, Accession No. brn 2803076, J. Org. Chem., 14: 1013, 1018 (1949).
Beilstein Database, Beilstein Institute for Organic Chemistry, Frankfurt an Main, DE, retrieved from XFIRE, Accession No. brn 3199913, Chem. Ber., 46: 3978 (1913).
Beilstein Database, Beilstein Institute for Organic Chemistry, Frankfurt an Main, DE, retrieved from XFIRE, Accession No. brn 3200601, J. Chem. Soc., pp. 104, 111 (1935).
Beilstein Database, Beilstein Institute for Organic Chemistry, Frankfurt an Main, DE, retrieved from XFIRE, Accession No. brn 3268495, Justus Liebigs Ann. Chem., 463:60 (1924).
Beilstein Database, Beilstein Institute for Organic Chemistry, Frankfurt an Main, DE, retrieved from XFIRE, Accession No. brn 3296969, Chem. News J. Ind. Sci, 36: 269 (1877).
Beilstein Database, Beilstein Institute for Organic Chemistry, Frankfurt an Main, DE, retrieved from XFIRE, Accession No. pcrn 859019, U.S. Pat. No. 4,429,152 A (Jan. 1984).
Beilstein Database, Beilstein Institute for Organic Chemistsry, Frankfurt an Main, DE, retrieved from XFIRE, Accession No. brn 3199917, Chem. Ber., 46: 288 (1913).
Beilstein Database, Beilstsein Institute for Organic Chemistry, Frankfurt an Main, DE, retrieved from XFIRE, Accession No. brn 3242057, Chem. Ber., 74: 500, 517 (1941).
Beilstein Database, Beistein Institut zur Forderung der Chemischen Wissenschaften, Frankfurt an Main, DE, XP002413837, Accession No. 2367395, Chem. Ber., 87: 179-181 (1954.).
Beilstein Database, Beistein Institut zur Forderung der Chemischen Wissenschaften, Frankfurt an Main, DE, XP002413838, Accession No. 2839685, J. Am. Chem Soc., 73: 903-904 (1951).
Beilstein Database, Beistein Institut zur Forderung der Chemischen Wissenschaften, Frankfurt an Main, DE, XP002413840, Accession No. 3031462, Bull Soc. Chim Belg., 61: 310-320 (1952).
Beilstein Database, Beistein Institut zur Forderung der Chemischen Wissenschaften, Frankfurt an Main, DE, XP002413842, Accession No. 3259704, Justus Liebigs Ann Chem, 429: 173 (1922).
Beilstein Database, Beistein Institut zur Förderung der Chemischen Wisssenschaften, Frankfurt an Main, DE, XP002413836, Accession No. 1869425, J. Labelled Compd Radiopharm, 44: S225-S227 (2001).

Beilstein Database, Beisten Insstitut zur Forderung der Chemischen Wissenschaften, Frankfurt an Main, DE, XP002413843, Accession No. 3530419, Justus Liebigs Ann Chem, 429: 164 (1922).
Beilstein Database, Beisten Institut zur Forderung der Chemischen Wissenschaften, Frankfurt an Main, DE, XP002413841, Accession No. 2641495, J. Org. Chem., 27: 3283-3295 (1962).
Bickers, et al. (2006) "Oxidative Stress in the Pathogenesis of Skin Disease," J. Investigatrive Dermatology, 126:2565-2575.
Bongartz et al., "Treatment of active psoriatic arthritis with the PPARγ ligand pioglitazone: an open-label pilot study", Rheumatology, 44:126-129 (2005).
Broadwith, P. (2009) "Enzyme Binds Both Sides of the Mirror," Chemistry World, pp. 1-2.
Brown et al., "Chimie Organique," C.R. Acad. Sc. Paris, t. (1978) 287:125-128.
Brunton, V.G., et al. (1997) "A Role of Epidermal Growth Factor Receptor, c-Syr and Focal Adhesion Kinase in an in vitro Model for the Progression of Colon Cancer," Oncogene, 14: 283-293.
Bull, A.W. (2003) "The Role of Perisome Proliferator-Activated Receptor γ in Colon Cancer and Inflammatory Bowel Disease," Arch Pathol Lab Med. 127: 1121-1123.
Clark, M., et al. (1989) "Validation of the General Purpose Tripos 5.2 Field," J. Comput Chem., 10: 982-1012.
Collino et al. (2006) "Modulation of the Oxidative Stress and Inflammatory Response by PPAR-gamma Agonists in the Hippocampus of Rats Exposed to Cerebral Ischemia/Reperfusion," European Journal of Pharmacology, Elsevier Science, NL, 530:70-80.
Corse et al., (1948) "Biosynthesis of penicillins" J. Am. Chem. Soc., 70(9):2837-2843, XP002330829.
Database CA [Online] Chemical Abstracts Service, Columbus Ohio, US; Database Accession No. 67:50608, Abstract of Baker et al.: "Irreversible Enzyme Inhibitors. LXXXVII. Hydrophobic Bonding to dihydrofolic reductase. 9. Mode of Binding of m-aryloxyalkyl groups on, 6-diamino-1,2-dihydro-2,2-dimethyl-1-phenyl-s-triazine", (1967).
Database CA [Online] Chemical Abstracts Service, Columbus, Ohio, US, Baroni, Sergio et al., "Compounds for the selective treatment of intestinal", Document No. 152:343527, Accession No. 2010:351508 CAPLUS (Giuliani International Ltd., Italy) (2007).
Database CA [Online] Chemical Abstracts Service, Columbus, Ohio, US, Database Accession No. 107:235800, Abstract of Cleary, et al., "Methylenecyclopropane rearrangement as a probe for free radical substituent effects. . sigma. . bul. Values for commonly encountered conjugating and organometallic groups", (1987).
Database CA [Online] Chemical Abstracts Service, Columbus, Ohio, US, Database Accession No. 111:153586, Abstract of Gonzalez, et al., ".alpha.-Amino carbanions. A second generation formamidine for facile deprotonation leading to .alpha.-quaternary substitution", (1989).
Database CA [Online] Chemical Abstracts Service, Columbus, Ohio, US, Database Accession No. 119:95018, Abstract of Yoon, et al., "Reduction of nitro compounds with borohydride exchange resin—nickel acetate", (1993).
Database CA [Online] Chemical Abstracts Service, Columbus, Ohio, US, Database Accession No. 131:144358, Abstract of Lamy-Pitara et al., "Selective Catalytic Hydrogenation of Unsaturated Derivatives of Nitrobenzene in Alcoholic Media", (1999).
Database CA [Online] Chemical Abstracts Service, Columbus, Ohio, US, Database Accession No. 50:52519, Abstract of Pratt, et al., "Reaction rates by distillation. VI. The etherification of benzyl and related alcohols", (1956).
Database CA [Online] Chemical Abstracts Service, Columbus, Ohio, US, Database Accession No. 8:526, Abstract of Schepss, "Electrolytic reduction of aldehydes", (1914).
Database CA [Online] Chemical Abstracts Service, Columbus, Ohio, US, Database Document No. 118:101608, Accession No. 1993:101608, Abstract of Breuer, et al., "An efficient synthesis of ethyl 3'-aminocinnamate", (1992).
Database CA [Online] Chemical Abstracts Service, Columbus, Ohio, US: Database Accession No. 96:19761, Abstract of Macek et al., "Studies on Local Anesthetics LXXIV. Basic esters of o-(m-) (alkoxymethyl)carbanilic acids", (1981).
Database CA [Online] Chemical Abstracts Service, Columbus, Ohio, US; Database Accession No. 105:24135, Abstract of Wulff, et

(56) References Cited

OTHER PUBLICATIONS al., "Chemistry of binding sites. VI. On the suitability of various aldehydes and ketones as binding sites for monoalcohols", (1986).
Database CA [Online] Chemical Abstracts Service, Columbus, Ohio, US; Database Accession No. 110:194186, Abstract of Pei et al., "A Lewis acid catalyst supported by polymers-styrene-methyl methacrylate copolymer-titanium tetrachloride complex preparation and uses in organic synthesis", (1989).
Database CA [Online] Chemical Abstracts Service, Columbus, Ohio, US; Database Accession No. 112:157479, Abstract of Joshi et al., "Catalysis by heteropoly acids: some new aspects", (1989).
Database CA [Online] Chemical Abstracts Service, Columbus, Ohio, US; Database Accession No. 121:204747, Abstract of Yang et al., "Photosolvolysis of 2-aminobenzyl alcohol in aqueous solution", (1994).
Database CA [Online] Chemical Abstracts Service, Columbus, Ohio, US; Database Accession No. 131:228419, "The Decomposition of methyl hemiacetals of benzaldehyde in aqueous solution: a study of the effect of aromatic substitution", (1999).
Database CA [Online] Chemical Abstracts Service, Columbus, Ohio, US; Database Accession No. 135:180359, Abstract of Pitts et al., "Indium metal as a reducing agent in organic synthesis", (2001).
Database CA [Online] Chemical Abstracts Service, Columbus, Ohio, US; Database Accession No. 49:68907, Abstract of Mann, et al., "The action of magnesium and of Grignard reagents on certain benzyl ethers. II. The action of Grignard reagents on .omicron.-, m-, and p-(methoxy- and phenoxymethyl) anilines", (1954).
Database CA [Online] Chemical Abstracts Service, Columbus, Ohio, US; Database Accession No. 66:37529, Abstract of Minisci, et al., "Orientation in the radical amination of aromatic compounds with N-chlorodimethylamine-competition between nuclear and benzylic attack", (1966).
Database CA [Online] Chemical Abstracts Service, Columbus, Ohio, US; Database Accession No. 84:4573, Abstract of Gale, et al., "Amidomethylation of some N,N-dialkylanilines (Tscherniac-Einhorn reaction)", (1975).
Database Caplus Chemical Abstracts Service, Columbus, Ohio, US; Database Accession No. 1913:10241, Abstract of Heller: Berichte der Deutschen Chemischen Gesellschaft (1913), 46:280-294.
Database Caplus Chemical Abstracts Service, Columbus, Ohio, US; Database Accession No. 1949:23214, Abstract of Tomcsik et al.: Helvetica Chimica Acta (1949), 32:31-34.
Database Caplus Chemical Abstracts Service, Columbus, Ohio, US; Database Accession No. 1955:19868, Abstract of Mann et al.: Chemistry & Industry (London, United Kingdom) (1954) 373-374.
Database Caplus Chemical Abstracts Service, Columbus, Ohio, US; Database Accession No. 1979:18291, Abstract of Brown et al.: "Affinity Chromatography of L-lactate dehydrogenase (LDH) on Synthetic Supports. Preparation and Immobilization of D- and L-p-aminophenyllactic Acids, New Effectors of LDH." Comptes Rendus des Seances de l'Academic des Scie.
Database Caplus Chemical Abstracts Service, Columbus, Ohio; Database Accession No. 1925:25469, Abstract of Sherwin: "Acetylation as a Physiologic Reaction." Proceedings of the Society for Experimental Biology and Medicine (1924), 22:182.
Database Caplus Chemical Abstracts Service, Columbus, Ohio; Database Accession No. 1967:490291, Abstract of Deljac et al.: "Absolute Configuration of (−−) -β-hydroxy-β-(m-hydroxyphenyl) propionic acid", Recueill des Travaux Chimiques des Pays-Bas (1967), 68(8):765-768.
Database Chemcats [Online] Chemical Abstracts Service, Columbus, Ohio, US; Accession No. 2058162244, Allichem Product List, Jun. 3, 2009; XP002591674, Feb. 6, 2008.
Database Registry (Online) Chemical Abstracts Service, Columbus, Ohio, US; Database Accession No. 1001756-73-5, Abstract & "Allichem Catalog" Jun. 3, 2009; XP002595814, Feb. 6, 2008.
Delbarre, F., et al., Chemical Abstracts, vol. 65, Columbus, Ohio, Abstract No. 93711, "Non-steroid antiinflammatory substances. I. Derivatives of the 4- and 5- aminosalicylic acids," (1964).

Deljac, A., et al., "Absolute Configuration of (−)-β-Hydroxy-β-(m)-Hydroxyphenyl)-Propionic Acid," Recueil des Travaux Chimiques des Pays-Bas, 86:765-768 (1967).
Dimon-Gadal et al. (2000) "Increased Oxidative Damage to Fibroblasts in Skin With and Without Lesions in Psoriasis," *Journal of Investigative Dermatology* 114:984-989.
DiPoï et al., "Epithelium-Mesenchyme Interactions Control the Activity of Peroxisome Proliferator-Activated Receptor β/δ during Hair Follicle Development", Mol. Cellular Biol., 2(5):1696-1712 (2005).
DiPoï et al., (2004) "Functions of Peroxisome Proliferator-Activated Receptors (PPAR) in Skin Homeostasis," *Lipids* 39 (11): 1093-1099.
Dubuquoy et al., "Impaired Expression of Peroxisome Proliferator-Activated Receptor Gamma in Ulcerative Colitis," Gastroenterology, 124:1265-1276 (2003).
Dubuquoy et al., "Role of peroxisome proliferator-activated receptor γ and retinoid X receptor heterodimer in hepatogastroenterological diseases," The Lancet, 360:1410-1418 (2002).
Egan et al., (2003) "Clinical pharmacology in inflammatory bowel disease: optimizing current medical therapy,"*Inflammatory Bowel Disease: From Bench to Bedside*, 2nd Edition, 495-521.
Ellis et al., "Placebo Response in Two Long-Term Randomized Psoriasis Studies that were Negative for Rosiglitazone", Am J Clin Dematol 8(2):93-102 (2007).
Examination Report dated Apr. 15, 2011 for Application No. 06 766 083.7-2103 (11 pages).
Fernholz et al., (1992) "Specificity of antibody-catalyzed transesterifications using enol esters: a comparison with lipase reactions" J. Org. Chem., 57:4756-4761, XP002330828.
Fuenzalida et al., (2007) "Peroxisome Proliferator-activated Receptor Gamma Up-regulates the Bcl-2 Anti-apoptotic Protein in Neurons and Induces Mitochondrial Stabilization and Proection against Oxidative Stress and Apoptosis," J. Biol. Chem., 282(51):37006-37015.
Gampe et al., (2000) "Asymmetry in the PPARγ/RXRα Crystal Structure Reveals the Molecular Basis of Heterodimerization Among Nuclear Receptors," Mol. Cell, 5:545-555.
Gerdes, J., et al., "Growth Fractions in Breast Cancers Determined in Situ with Monoclonal Antibody Ki-67," J. Clin. Pathol., 39: 977-80 (1986).
Gormin, D., "Picosecond Transient Absorption Spectra of Aminosalicylates in Confirmation of the Triple Excitation Mechanism," J. Phys. Chem, 1989, 93, p. 5979-5980.
Guo, et al., "Effect of Uyghur Compound Xipayi Kui Jie' an on the Ultrastructure of Small Intestinal Epithelial Cell in Rat Model of Ulcerative Colitis," Journal of Xinjiang Medical University (2009) 32 (7), p. 893-894.
Harari, P.M., "Epidermal Growth Factor Receptor Inhibition Strategies in Oncology," Endocr Relat Cancer, 11: 689-708 (2004).
Harrington et al., "A re-appraisal of lactose intolerance", Int J Clin Pract, 62(10):1541-1546 (2008).
Husova, Libuse, et al., "Hepatopathy, coeliac disease and lymphocytic colitis," Ceska A. Slovenska Gastroenterologie A. Hepatologie—Czech and Slovak Gastroenterology and Hepatology, 61 (6) (2007), 309-313.
International Preliminary Report on Patentability for PCT/IE2006/000076 mailed on Jan. 22, 2008.
International Preliminary Report on Patentability, with Written Opinion, issued on Jan. 22, 2008, in parent PCT Application No. PCT/IE2006/000078.
International Search Report and Written Opinion for PCT/IE2006/000078, mailed Jan. 26, 2007.
International Search Report for PCT/EP2008/052354, mailed Jun. 9, 2008.
International Search Report for PCT/EP2008/068265, mailed Aug. 11, 2009.
International Search Report for PCT/EP2009/008631, mailed Aug. 19, 2010.
International Search Report for PCT/EP2009/008633, mailed Feb. 22, 2010.
International Search Report for PCT/EP2010/000935 mailed on Aug. 23, 2010.

(56) References Cited

OTHER PUBLICATIONS

International Search Report for PCT/EP2010/000939 mailed on Sep. 20, 2010.
International Search Report for PCT/EP2013/052617, mailed Aug. 21, 2013.
International Search Report for PCT/EP2013/057729, mailed Jun. 11, 2013.
International Search Report for PCT/EP2013/069062, mailed Dec. 10, 2013.
International Search Report for PCT/EP2013/069063, mailed Dec. 20, 2013.
International Search Report issued on Feb. 1, 2007 for PCT/IE2006/000076.
Ireland et al. (1992) "Comparison of 5-aminosalicylic acid and N-acetylaminosalicylic acid uptake by the isolated human colonic epithelial cell," *Gut* 33:1343-1347.
Janda et al., (1988) "Antibody catalysis of bimolecular amide formation" J. Am. Chem. Soc., 110:4835-4837, XP002330827.
Johnson et al., "Intestinal Fibrosis Is Reduced by early Elimination of Inflammation in a Mouse Model of IBD: Impact of a "Top-Down" Approach to Intestinal Fibrosis in Mice", Inflamm Bowel Dis, 18(3):460-471 (2012).
Jones, G., et al., "Development and Validation of a Genetic Algorithm for Flexible Docking," J. Mol. Biol., 267: 727-748 (1997).
Kari, C., et al., "Targeting the Epidermal Growth Factor Receptor in Cancer: Apoptosis Takes Center Stage," Cancer Res., 63: 1-5 (2003).
Koeffler, H.P., "Peroxisome Proliferator-activated Receptpr γ and Cancers," Clinical Cancer Research, 9: 1-9 (2003).
Kuenzli et al., "Effect of Topical PPARβ/δ and PPARγ Agonists on Plaque Psoriasis: A Pilot Study", Dermatology, 206:252-256 (2003).
Liao, Yun-Zhang, et al., (1990) "Therapeutic Effect of Methyl 5-Aminosalicylate on Experimental Ulcerative Colitis in Rabbits," Acta Pharmacologica Sinica, 11(1): 54-56.
Lin et al., (1998) "An antibody transesterase derived from reactive immunization that utilizes a wide variety of alcohol substrates," Chem. Commun., pp. 1075-1076, XP00904865.
Lowe, D. (2009) "More Binding Site Weirdness," Corante: In the Pipeline, pp. 1-4.
Mager, Von P.P., et al., "Struktur-Wirkungs-Beziehungen bei Salizylsaure- und Benzoesaurederivaten," Zbl. Pharm. 118 (1979) Heft 12, p. 1259-1275.
Mangelsdorf, D.J., et al., "The Nuclear Receptor Superfamily: The Second Decade," Cell, 83: 835-839 (Dec. 1995).
Meek, W., et al., "Carboxylation of Substituted Phenols in N,N-Dimethylamide Solvents at Atmospheric Pressure," Journal of Chemical and Engineering Data, vol. 14, No. 3, 1969, p. 388-391.
Mendelsohn, J., "The Epidermal Growth Factor Receptor as a Target for Cancer Therapy," Endocr Relat Cancer, 8: 3-9 (2001).
Merck Manual Home Edition, "Ulcerative Colitis", Merck Sharp & Dohme Corp., Copyright © 2004-2011, pp. 1-6.
Michalik, et al. (2007) "Peroxisome Proliferator-activated Receptors (PPARs) in Skin Health, Repair and Disease," *Biochimica et Biophysica Acta* 1771:991-998.
Misra, P., et al., "Phosphorylation of Transcriptional Coactivator Peroxisome Proliferator-Activated Receptor (PPAR)-Binding Protein (PBP). Stimulation of Transcriptional Regulation by Mitogen-Activated Protein Kinase," J. Biol. Chem., 277: 48745-48754 (2002).
Nolte, R.T., et al., "Ligand Binding and Co-Activator Assembly of the Peroxisome Proliferator-Activated Receptor-γ," Nature, 395: 137-143 (Sep. 1988).
O'Mahony, et al., (1990) Postgraduate Medical Journal, 66(773), pp. 238-241.
Office Action issued in Japanese Patent Application No. 2011-549494 mailed Feb. 25, 2014, and its English translation (8 pages).

Osawa, E., et al., "Peroxisome Proliferator-Activated Receptor γ Ligands Suppress Colon Carcinogenesis Induced by Azoxymethane in Mice," Gastroenterology, 124: 361-367 (2003).
Pedersen et al., "Topical rosiglitazone treatment improves ulcerative colitis by restoring peroxisome proliferator-activated receptor-gamma activity", Am J Gastroenterol, 105(7):1596-1603 (2010). Abstract only.
Peyrin-Biroulet, L., et al. (2007) "Peroxisome Proliferator-Activated Receptor Gamma Functions as an Antibacterial Factor," Journal of Crohn's and Colitis Supplements, 1(1), p. 2.
Ponchant, M., et al., Synthesis of 5-[$^{125}$I]-Iodo-Zacopride, a New Probe for 5-HT$_3$ Receptor Binding Sites, Journal of Labelled Compounds and Radiopharmaceuticals, vol. XXIX, No. 10, 1991, p. 1147-1155.
Reifen, Ram, et al. (2004) "5-ASA and Lycopene Decrease the Oxidative Stress and Inflammation Induced by Iron in Rats with Colitis," J. Gastroenterol, 39: 514-519.
Risérus, Ulf, et al., (2008) "Activation of Peroxisome Proliferator-activated Receptor (PPAR) Delta Promotes Reversal of Multiple Metabolic Abnormalities, Reduces Oxidative Stress, and Increases Fatty Acid Oxidation in Moderately Obese Men," Diabetes 57, NR. 2, 332-339.
Ritland et al., (1999) "Evaluation of 5-Aminosalicylic Acid (5-ASA) for Cancer Chemoprevention: Lack of Efficacy against Nascent Adenomatous Polyps in the Apc$^{Min}$ Mouse," Clinical Cancer Research, 5(4)855-863.
Robertson D., et al., "Structure-Activity Relationships of Arylimidazopyridine Cardiotonics: Discovery and Inotropic Activity of 2-[2-Methoxy-4-(methylsulfinyl)phenyl]-1H-imidazo[4,5-c]pyridine," J. Med. Chem. 1985, 28, p. 717-727.
Rousseaux, C., et al., Intestinal Anti-inflammatory Effect of 5-Aminosalicylic Acid is Dependent on Peroxisome Proliferator-Activated Receptor-γ, JEM 201(8): 1205-1215 (2005).
Rovner, S. (2009) "An Enzyme Reveals an Unexpected Inclusiveness, Protein Binding: Bacterial Enzyme's Active Site Welcomes Both Enantiomers of a Chiral Molecule at the Same Time," Chemical & Engineering News, pp. 1-2.
Schauber, Jurgen, et al. (2004) "Histone-Deacetylase Inhibitors Induce the Cathelicidin LL-37 in Gastrointentinal Cells," Molecular Immunology, 41(9): 847-854.
Schwab, Markus, et al. (2007) "Role of Nuclear Hormone Receptors in Butyrate-Mediated Up-Regulation of the Antimicrobial Peptide Cathelicidin in Epithelial Colorectal Cells," Molecular Immunology, 44(8): 2107-2114.
Sherwin, C.P., "Acetylation as a Physiologic Reaction," Scientific Proceedings (1924), 22, 182.
Tanaka, T., et al., "Ligands for Peroxisome Proliferator-Activated Receptors α and γ Inhibit Chemically Induced Colitis and Formation of Aberrant Crypt Foci in Rats," Cancer Res., 61: 2424-2428 (2001).
Tosti et al., "Treatment strategies for alopecia", Expert Opin Pharmacother, 10(6):1017-1026 (2009).
Tuleu, et al., "Colonic delivery of 4-aminosalicylic acid using amylose-ethyl cellulose-coated hydroxypropyl methyl cellulose capsules," Aliment Pharmacol Ther., (2002); 167: 1771-1779.
van't Riet, Bart, et al. (1979) "Synthesis of Hydroxy and Amino-Substituted Benzohydroxamic Acids: Inhibition of Ribonucleotide Reductase and Antitumor Activity," Journal of Medicinal Chemistry, 22(5): 589-592.
Venkatraman et al., "Alpha-Lipoic acid-based PPARgamma agonists for treating inflammatory skin diseases", Arch Dermatol Res, 296(3):97-104 (2004). Abstract only.
Wang, R., et al., "Further Development and Validation of Emphirical Scoring Functions for Structure-Based Binding Affinity Prediction," J. Comput. Aided Mol. Des., 16: 11-26 (2002).
Wang, Tian-Tian, et al. (2004) "Cutting Edge: 1,25-Dihydroxyvitamin D3 is a Direct Inducer of Antimicrobial Peptide Gene Expression," The Journal of Immunology, 173: 2909-2912.

(56) References Cited

OTHER PUBLICATIONS

Westin, S., et al., "Interactions Controlling the Assembly of Nuclear-Receptor Heterodimers and Co-Activators," Nature, 395: 199-202 (Sep. 1998).

Williams, J.G., et al. (1989) "Effect of Sulphasalazine and its Active Metabolite, 5-Amino-Salicylic Acid, on Toxic Oxyden Metabolite Production by Neutrophils," Gut, 30: 1581-1587.

Written Opinion of the International Searching Authority for PCT/IE2006/000076 mailed Feb. 1, 2007.

Xu, H.E., et al., "Structural Determinants of Ligand Binding Selectivity Between the Peroxisome Proliferator-Activated Receptors," Proc. Natl. Acad. Sci. U.S.A., 98: 13919-13924 (2001).

Yanai, K., et al., "Para-Position Derivatives of Fungal Anthelmintic Cyclodepsipeptides Engineered with Streptomyces Venezuelae Antibiotic Biosynthetic Genes," Nature Biotechnology (2004) 22, 848-855.

Youssef, J., et al., "Role of Peroxisome Proliferator-Activated Receptors in Inflammation Control," J. Biomed Biotechnol. 3: 156-166 (2004).

Zhou et al. (1999) "Intestinal Metabolism and Transport of 5-Aminosalicylate," *Drug Metab Dispos* 27(4)479-485.

ALKYLAMIDO COMPOUNDS AND USES THEREOF

This application is a continuation of U.S. Ser. No. 13/201,786, filed Nov. 17, 2011, which is a national stage filing under 35 U.S.C. 371 of PCT/EP2010/000935, filed Feb. 16, 2010, which claims priority to EP09425056.0, filed Feb. 16, 2009; U.S. Ser. No. 61/179,062, filed May 18, 2009, and U.S. Ser. No. 61/287,461, filed Dec. 17, 2009, each of which is incorporated by reference in its entirety.

BACKGROUND

Peroxisome Proliferator Activated Receptors (PPARs) are members of the nuclear hormone receptor super family, which are ligand-activated transcription factors regulating gene expression. Certain PPARs play roles in the regulation of cell differentiation, development and metabolism of higher organisms.

Three types of PPAR has been identified: alpha, expressed in the liver, kidney, heart and other tissues and organs, beta/delta expressed for example in the brain, and gamma, expressed in three forms: gamma1, gamma2, and gamma3. PPARγ receptors have been associated with a number of disease states including dyslipidemia, hyperlipidemia, hypercholesteremia, atherosclerosis, atherogenesis, hypertriglyceridemia, heart failure, myocardial infarction, vascular diseases, cardiovascular diseases, hypertension, obesity, inflammation, arthritis, cancer, Alzheimer's disease, skin disorders, respiratory diseases, ophthalmic disorders, IBDs (irritable bowel disease), ulcerative colitis and Crohn's disease.

Further, treatment of tumor cells with ligands of PPARγ receptors can induce a decrease in cellular proliferation, cell differentiation and apoptosis, and therefore may be useful in preventing carcinogenesis. Intestinal anti-inflammatory activity may be dependent on binding and subsequent activation of PPARγ receptors.

In addition, numerous studies have indicated that EGF receptor inhibitors may control proliferation and spread of tumors.

Accordingly, molecules that modulate the activity of PPARs and/or EGF receptors are useful as therapeutic agents in the treatment of such diseases.

SUMMARY

This disclosure is generally directed to compounds which may be specific to PPAR receptors and/or EGF receptors, and their use as, for example, medicinal agents. Also provided are pharmaceutical compositions comprising at least one disclosed compound, or pharmaceutically acceptable salt or N-oxide thereof, and a pharmaceutically acceptable carrier.

One embodiment provides compounds represented by formula I, and compositions comprising such compounds:

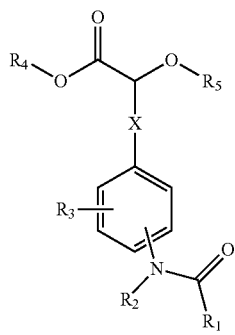

I wherein X is $C_1$-$C_3$alkylene, optionally substituted with one, two or three substituents selected from halogen or hydroxyl;

$R_1$ is selected from the group consisting of $C_1$-$C_6$alkyl, $C_3$-$C_6$cycloalkyl, $C_2$-$C_6$alkenyl, and $C_2$-$C_6$alkynyl;

$R_2$ is selected from the group consisting of hydrogen and $C_1$-$C_6$alkyl;

$R_3$ is independently selected, for each occurrence from the group consisting of hydrogen, $C_1$-$C_6$alkoxy, $C_1$-$C_6$alkyl, cyano, $C_3$-$C_6$cycloalkyl, halogen, hydroxyl, and nitro;

$R_4$ is selected from the group consisting of hydrogen and $C_1$-$C_6$alkyl;

$R_5$ is hydrogen or $C_1$-$C_6$alkyl;

or pharmaceutically acceptable salts or N-oxides thereof.

Another embodiment provides compounds represented by formula II, and compositions comprising such compounds:

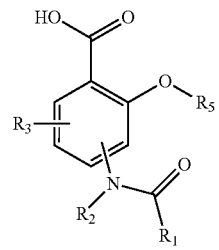

II wherein $R_1$ is selected from the group consisting of $C_1$-$C_6$alkyl, $C_3$-$C_6$cycloalkyl, $C_2$-$C_6$alkenyl, and $C_2$-$C_6$alkynyl;

$R_2$ is selected from the group consisting of hydrogen and $C_1$-$C_6$alkyl;

$R_3$ is independently selected, for each occurrence from the group consisting of hydrogen, $C_1$-$C_6$alkoxy, $C_1$-$C_6$alkyl, cyano, $C_3$-$C_6$cycloalkyl, halogen, hydroxyl, and nitro;

$R_5$ is $C_1$-$C_6$alkyl;

or pharmaceutically acceptable salts or N-oxides thereof.

Also provided herein are methods of treating cancer (e.g. colorectal cancer) such as tumors expressing PPAR receptors and/or EGF receptors, comprising administering to a subject in need thereof a therapeutically effective amount of a compound of formula I or II, or a pharmaceutically acceptable salt or N-oxides thereof. Also contemplated herein are compositions that include a compound represented by formula I or II and e.g., a pharmaceutically acceptable excipient.

Also provided are compounds represented by formulas I and II for use in therapy and/or for the manufacture of a medicament for the treatment of cancer such as colorectal cancer.

DETAILED DESCRIPTION

Figure 1:
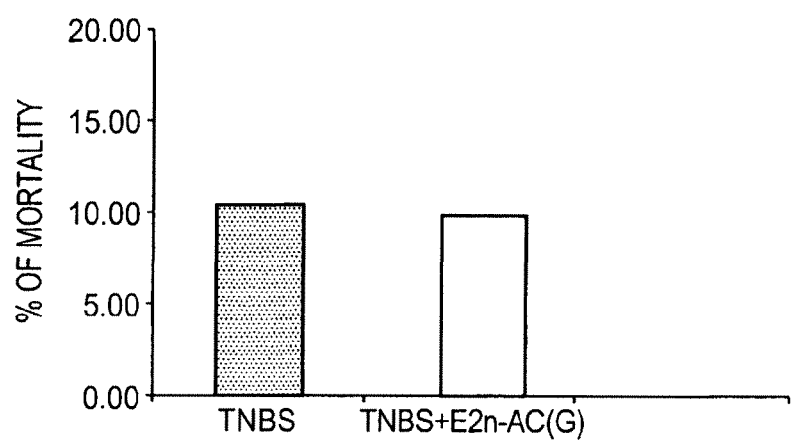
FIG. 1 depicts the % mortality of mice receiving TNBS (trinitrobenzene sulfonic acid) versus mice receiving TNBS and N-acetyl E2 in a murine colitis model.

The features and other details of the disclosure will now be more particularly described. Before further description of the present invention, certain terms employed in the specification, examples and appended claims are collected here. These definitions should be read in light of the remainder of the disclosure and understood as by a person of skill in the art. Unless defined otherwise, all technical and scientific terms used herein have the same meaning as commonly understood by a person of ordinary skill in the art.

DEFINITIONS

"Treating" includes any effect, e.g., lessening, reducing, modulating, or eliminating, that results in the improvement of the condition, disease, disorder and the like.

The term "alkenyl" as used herein refers to an unsaturated straight or branched hydrocarbon having at least one carbon-carbon double bond, such as a straight or branched group of 2-12, 2-10, or 2-6 carbon atoms, referred to herein as $C_2$-$C_{12}$alkenyl, $C_2$-$C_{10}$alkenyl, and $C_2$-$C_6$alkenyl, respectively. Exemplary alkenyl groups include, but are not limited to, vinyl, allyl, butenyl, pentenyl, hexenyl, butadienyl, pentadienyl, hexadienyl, 2-ethylhexenyl, 2-propyl-2-butenyl, 4-(2-methyl-3-butene)-pentenyl, etc.

The term "alkoxy" as used herein refers to an alkyl group attached to an oxygen (—O-alkyl-). Exemplary alkoxy groups include, but are not limited to, groups with an alkyl, alkenyl or alkynyl group of 1-12, 1-8, or 1-6 carbon atoms, referred to herein as $C_1$-$C_{12}$alkoxy, $C_1$-$C_8$alkoxy, and $C_1$-$C_6$alkoxy, respectively. Exemplary alkoxy groups include, hut are not limited to methoxy, ethoxy, etc. Similarly, exemplary "alkenoxy" groups include, but are not limited to vinyloxy, allyloxy, butenoxy, etc.

The term "alkyl" as used herein refers to a saturated straight or branched hydrocarbon, such as a straight or branched group of 1-12, 1-10, or 1-6 carbon atoms, referred to herein as $C_1$-$C_{12}$alkyl, $C_1$-$C_{10}$alkyl, and $C_1$-$C_6$alkyl, respectively. Exemplary alkyl groups include, but are not limited to, methyl, ethyl, propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, pentyl, isopentyl, neopentyl, hexyl, heptyl, octyl, etc. In certain embodiments, alkyl refers to $C_1$-$C_6$ alkyl. In certain embodiments, cycloalkyl refers to $C_3$-$C_6$cycloalkyl.

Alkyl, alkenyl and alkynyl groups can, in some embodiments, be optionally be substituted with or interrupted by at least one group selected from alkanoyl, alkoxy, alkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl and thiocarbonyl.

The term "alkynyl" as used herein refers to an unsaturated straight or branched hydrocarbon having at least one carbon-carbon triple bond, such as a straight or branched group of 2-12, 2-8, or 2-6 carbon atoms, referred to herein as $C_2$-$C_{12}$alkynyl, $C_2$-$C_8$alkynyl, and $C_2$-$C_6$alkynyl, respectively. Exemplary alkynyl groups include, but are not limited to, ethynyl, propynyl, butynyl, pentynyl, hexynyl, methylpropynyl, 4-methyl-1-butynyl, 4-propyl-2-pentynyl, and 4-butyl-2-hexynyl, etc.

The term "amide" or "amido" as used herein refers to a radical of the form —$R_a$C(O)N($R_b$)—, —$R_a$C(O)N($R_b$) $R_c$—, or —C(O)N$R_b$$R_c$, wherein $R_a$, $R_b$ and $R_c$ are each independently selected from alkoxy, alkyl, alkenyl, alkynyl, amide, amino, aryl, arylalkyl, carbamate, cycloalkyl, ester, ether, formyl, halogen, haloalkyl, heteroaryl, heterocyclyl, hydrogen, hydroxyl, ketone, and nitro. The amide can be attached to another group through the carbon, the nitrogen, $R_b$, $R_c$, or $R_a$. The amide also may be cyclic, for example $R_b$ and $R_c$, $R_a$ and $R_b$, or $R_a$ and $R_c$ may be joined to form a 3- to 12-membered ring, such as a 3- to 10-membered ring or a 5- to 6-membered ring. The term "carboxamido" refers to the structure —C(O)N$R_b$$R_c$.

The term "amidino" as used herein refers to a radical of the form —C(=NR)NR'R" where R, R', and R" can each independently be selected from alkyl, alkenyl, alkynyl, amide, aryl, arylalkyl, cyano, cycloalkyl, haloalkyl, heteroaryl, heterocyclyl, hydroxyl, ketone and nitro.

The term "amine" or "amino" as used herein refers to a radical of the form —N$R_d$$R_e$, —N($R_d$)$R_e$—, or —$R_e$N($R_d$) $R_f$— where $R_d$, $R_e$, and $R_f$ are independently selected from alkoxy, alkyl, alkenyl, alkynyl, amide, amino, aryl, arylalkyl, carbamate, cycloalkyl, ester, ether, formyl, halogen, haloalkyl, heteroaryl, heterocyclyl, hydrogen, hydroxyl, ketone, and nitro. The amino can be attached to the parent molecular group through the nitrogen, $R_d$, $R_e$ or $R_f$. The amino also may be cyclic, for example any two of Rd, Re or Rf may be joined together or with the N to form a 3- to 12-membered ring, e.g., morpholino or piperidinyl. The term amino also includes the corresponding quaternary ammonium salt of any amino group, e.g., —[N(Rd)(Re)(Rf)]+. Exemplary amino groups include aminoalkyl groups, wherein at least one of $R_d$, $R_e$, or $R_f$ is an alkyl group.

The term "aryl" as used herein refers to refers to a mono-, bi-, or other multi-carbocyclic, aromatic ring system. In certain embodiments, aryl refers to a monocyclic and/or bicyclic, 5 to 6 membered ring. The aromatic ring may be substituted at one or more ring positions with substituents selected from alkanoyl, alkoxy, alkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl and thiocarbonyl. The term "aryl" also includes polycyclic ring systems having two or more cyclic rings in which two or more carbons are common to two adjoining rings (the rings are "fused rings") wherein at least one of the rings is aromatic, e.g., the other cyclic rings may be cycloalkyls, cycloalkenyls, cycloalkynyls, and/or aryls. Exemplary aryl groups include, but are not limited to, phenyl, tolyl, anthracenyl, fluorenyl, indenyl, azulenyl, and naphthyl, as well as benzo-fused carbocyclic moieties such as 5,6,7,8-tetrahydronaphthyl.

The term "arylalkyl" as used herein refers to an aryl group having at least one alkyl substituent, e.g. -aryl-alkyl-. Exemplary arylalkyl groups include, but are not limited to, arylalkyls having a monocyclic aromatic ring system, wherein the ring comprises 6 carbon atoms. For example, "phenylalkyl" includes phenyl$C_4$alkyl, benzyl, 1-phenylethyl, 2-phenylethyl, etc.

The term "carbonyl" as used herein refers to the radical —C(O)—.

The term "carboxamido" as used herein refers to the radical —C(O)NRR', where R and R' may be the same or different. R and R' may be selected from, for example, alkyl, aryl, arylalkyl, cycloalkyl, formyl, haloalkyl, heteroaryl and heterocyclyl.

The term "carboxy" as used herein refers to the radical —COOH or its corresponding salts, e.g. —COONa, etc.

The term "cyano" as used herein refers to the radical —CN.

The term "cycloalkoxy" as used herein refers to a cycloalkyl group attached to an oxygen.

The term "cycloalkyl" as used herein refers to a monovalent saturated or unsaturated cyclic, bicyclic, or bridged bicyclic hydrocarbon group of 3-12, 3-8, 4-8, or 4-6 carbons, referred to herein, e.g., as "$C_{4-8}$cycloalkyl," derived from a cycloalkane. Exemplary cycloalkyl groups include, but are not limited to, cyclohexanes, cyclohexenes, cyclopentanes, cyclopentenes, cyclobutanes and cyclopropanes. Cycloalkyl groups may be substituted with alkanoyl, alkoxy, alkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl and thiocarbonyl. Cycloalkyl groups can be fused to other cycloalkyl, aryl, or heterocyclyl groups. In certain embodiments, cycloalkyl refers to $C_3$-$C_6$ alkyl.

The terms "halo" or "halogen" or "Hal" as used herein refer to F, Cl, Br, or I.

The term "haloalkyl" as used herein refers to an alkyl group substituted with one or more halogen atoms.

The term "nitro" as used herein refers to the radical —$NO_2$.

The term "phenyl" as used herein refers to a 6-membered carbocyclic aromatic ring. The phenyl group can also be fused to a cyclohexane or cyclopentane ring. Phenyl can be substituted with one or more substituents including alkanoyl, alkoxy, alkyl, alkenyl, alkynyl, amido, amidino, amino, aryl, arylalkyl, azido, carbamate, carbonate, carboxy, cyano, cycloalkyl, ester, ether, formyl, halogen, haloalkyl, heteroaryl, heterocyclyl, hydroxyl, imino, ketone, nitro, phosphate, phosphonato, phosphinato, sulfate, sulfide, sulfonamido, sulfonyl and thiocarbonyl.

The term "phosphate" as used herein refers to the radical —OP(O)(O$R_{aa}$)$_2$ or its anions. The term "phosphanate" refers to the radical —P(O)(O$R_{aa}$)$_2$ or its anions. The term "phosphinate" refers to the radical —P$R_{aa}$(O)(O$R_{aa}$) or its anion, where each $R_{aa}$ can be selected from, for example, alkyl, alkenyl, alkynyl, aryl, arylalkyl, cycloalkyl, hydrogen, haloalkyl, heteroaryl, and heterocyclyl.

The term "pharmaceutically acceptable carrier" or "pharmaceutically acceptable excipient" as used herein refers to any and all solvents, dispersion media, coatings, isotonic and absorption delaying agents, and the like, that are compatible with pharmaceutical administration. The use of such media and agents for pharmaceutically active substances is well known in the art. The compositions may also contain other active compounds providing supplemental, additional, or enhanced therapeutic functions.

The term "pharmaceutical composition" as used herein refers to a composition comprising at least one compound as disclosed herein formulated together with one or more pharmaceutically acceptable carriers.

"Individual," "patient," or "subject" are used interchangeably and include to any animal, including mammals, preferably mice, rats, other rodents, rabbits, dogs, cats, swine, cattle, sheep, horses, or primates, and most preferably humans. The compounds of the invention can be administered to a mammal, such as a human, but can also be other mammals such as an animal in need of veterinary treatment, e.g., domestic animals (e.g., dogs, cats, and the like), farm animals (e.g., cows, sheep, pigs, horses, and the like) and laboratory animals (e.g., rats, mice, guinea pigs, and the like). The mammal treated in the methods of the invention is desirably a mammal in whom modulation of PPAR and/or EGF receptors is desired. "Modulation" includes antagonism (e.g., inhibition), agonism, partial antagonism and/or partial agonism.

In the present specification, the term "therapeutically effective amount" means the amount of the subject compound that will elicit the biological or medical response of a tissue, system, animal or human that is being sought by the researcher, veterinarian, medical doctor or other clinician. The compounds of the invention are administered in therapeutically effective amounts to treat a disease. Alternatively, a therapeutically effective amount of a compound is the quantity required to achieve a desired therapeutic and/or prophylactic effect, such as an amount which results in the prevention of or a decrease in the symptoms associated with a disease associated with PPAR and/or EGF receptors.

The term "pharmaceutically acceptable salt(s)" as used herein refers to salts of acidic or basic groups that may be present in compounds used in the present compositions. Compounds included in the present compositions that are basic in nature are capable of forming a wide variety of salts with various inorganic and organic acids. The acids that may be used to prepare pharmaceutically acceptable acid addition salts of such basic compounds are those that form non-toxic acid addition salts, i.e., salts containing pharmacologically acceptable anions, including but not limited to malate, oxalate, chloride, bromide, iodide, nitrate, sulfite, bisulfate, phosphate, acid phosphate, isonicotinate, acetate, lactate, salicylate, citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds included in the present compositions that include an amino moiety may form pharmaceutically acceptable salts with various amino acids, in addition to the acids mentioned above. Compounds included in the present compositions that are acidic in nature are capable of forming base salts with various pharmacologically acceptable cations. Examples of such salts include alkali metal or alkaline earth metal salts and, particularly, calcium, magnesium, sodium, lithium, zinc, potassium, and iron salts.

The compounds of the disclosure may contain one or more chiral centers and/or double bonds and, therefore, exist as stereoisomers, such as geometric isomers, enantiomers or diastereomers. The term "stereoisomers" when used herein consist of all geometric isomers, enantiomers or diastereomers. These compounds may be designated by the symbols "R" or "S," depending on the configuration of substituents around the stereogenic carbon atom. The present invention encompasses various stereoisomers of these compounds and mixtures thereof. Stereoisomers include enantiomers and diastereomers. Mixtures of enantiomers or diastereomers may be designated "(±)" in nomenclature, but the skilled artisan will recognize that a structure may denote a chiral center implicitly.

Individual stereoisomers of compounds of the present invention can be prepared synthetically from commercially available starting materials that contain asymmetric or stereogenic centers, or by preparation of racemic mixtures followed by resolution methods well known to those of ordinary skill in the art. These methods of resolution are exemplified by (1) attachment of a mixture of enantiomers to a chiral auxiliary, separation of the resulting mixture of diastereomers by recrystallization or chromatography and liberation of the optically pure product from the auxiliary, (2) salt formation employing an optically active resolving agent, or (3) direct separation of the mixture of optical enantiomers on chiral chromatographic columns. Stereoisomeric mixtures can also be resolved into their component stereoisomers by well known methods, such as chiral-phase gas chromatography, chiral-phase high performance liquid chromatography, crystallizing the compound as a chiral salt complex, or crystallizing the compound in a chiral solvent. Stereoisomers can also be obtained from stereomerically-pure intermediates, reagents, and catalysts by well known asymmetric synthetic methods.

Geometric isomers can also exist in the compounds of the present invention. The symbol ══ denotes a bond that may be a single, double or triple bond as described herein. The present invention encompasses the various geometric isomers and mixtures thereof resulting from the arrangement of substituents around a carbon-carbon double bond or arrangement of substituents around a carbocyclic ring. Substituents around a carbon-carbon double bond are designated as being in the "Z" or "E" configuration wherein the terms "Z" and "E" are used in accordance with IUPAC standards. Unless otherwise specified, structures depicting double bonds encompass both the "E" and "Z" isomers.

Substituents around a carbon-carbon double bond alternatively can be referred to as "cis" or "trans," where "cis" represents substituents on the same side of the double bond and "trans" represents substituents on opposite sides of the double bond. The arrangement of substituents around a carbocyclic ring are designated as "cis" or "trans." The term "cis" represents substituents on the same side of the plane of the ring and the term "trans" represents substituents on opposite sides of the plane of the ring. Mixtures of compounds wherein the substituents are disposed on both the same and opposite sides of plane of the ring are designated "cis/trans."

The compounds disclosed herein can exist in solvated as well as unsolvated forms with pharmaceutically acceptable solvents such as water, ethanol, and the like, and it is intended that the invention embrace both solvated and unsolvated forms. In one embodiment, the compound is amorphous. In one embodiment, the compound is a polymorph. In another embodiment, the compound is in a crystalline form.

The invention also embraces isotopically labeled compounds of the invention which are identical to those recited herein, except that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^2H$, $^3H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Certain isotopically-labeled disclosed compounds (e.g., those labeled with $^3H$ and $^{14}C$) are useful in compound and/or substrate tissue distribution assays. Tritiated (i.e., $^3H$) and carbon-14 (i.e., $^{14}C$) isotopes are particularly preferred for their case of preparation and detectability. Further, substitution with heavier isotopes such as deuterium (i.e., $^2H$) may afford certain therapeutic advantages resulting from greater metabolic stability (e.g., increased in vivo half-life or reduced dosage requirements) and hence may be preferred in some circumstances. Isotopically labeled compounds of the invention can generally be prepared by following procedures analogous to those disclosed in the e.g., Examples herein by substituting an isotopically labeled reagent for a non-isotopically labeled reagent.

The term "prodrug" refers to compounds that are transformed in vivo to yield a disclosed compound or a pharmaceutically acceptable salt, hydrate or solvate of the compound. The transformation may occur by various mechanisms, such as through hydrolysis in blood. For example, if a compound of the invention or a pharmaceutically acceptable salt, hydrate or solvate of the compound contains a carboxylic acid functional group, a prodrug can comprise an ester formed by the replacement of the hydrogen atom of the acid group with a group such as ($C_1$-$C_8$) alkyl, ($C_2$-$C_{12}$)alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N—($C_1$-$C_2$)alkylamino($C_2$-$C_3$)alkyl (such as β-dimethylaminoethyl), carbamoyl-($C_1$-$C_2$)alkyl, N,N-di($C_1$-$C_2$)alkylcarbamoyl-($C_1$-$C_2$)alkyl and piperidino-, pyrrolidino- or morpholino($C_2$-$C_3$)alkyl.

Similarly, if a compound or the invention contains an alcohol functional group, a prodrug can be formed by the replacement of the hydrogen atom of the alcohol group with a group such as $(C_1-C_6)$alkanoyloxymethyl, 1-$((C_1-C_6)$alkanoyloxy)ethyl, 1-methyl-1-$((C_1-C_6)$alkanoyloxy)ethyl $(C_1-C_6)$alkoxycarbonyloxymethyl, N—$(C_1-C_6)$alkoxycarbonylaminomethyl, succinoyl, $(C_1-C_6)$alkanoyl, α-amino $(C_1-C_4)$alkanoyl, arylacyl and α-aminoacyl, or α-aminoacyl-α-aminoacyl, where each α-aminoacyl group is independently selected from the naturally occurring L-amino acids, $P(O)(OH)_2$, —$P(O)(O(C_1-C_6)alkyl)_2$ or glycosyl (the radical resulting from the removal of a hydroxyl group of the hemiacetal form of a carbohydrate).

If a compound of the invention incorporates an amine functional group, a prodrug can be formed by the replacement of a hydrogen atom in the amine group with a group such as R-carbonyl, RO-carbonyl, NRR'-carbonyl where R and R' are each independently $(C_1-C_{10})$alkyl, $(C_3-C_7)$cycloalkyl, benzyl, or R-carbonyl is a natural α-aminoacyl or natural α-aminoacyl-natural α-aminoacyl, —$C(OH)C(O)OY^1$ wherein $Y^1$ is H, $(C_1-C_6)$alkyl or benzyl, —$C(OY^2)Y^3$ wherein $Y^2$ is $(C_1-C_4)$alkyl and $Y^3$ is $(C_1-C_6)$alkyl, carboxy$(C_1-C_6)$alkyl, amino$(C_1-C_4)$alkyl or mono-N- or di-N,N—$(C_1-C_6)$alkylaminoalkyl, $C(Y^4)Y^5$ wherein $Y^4$ is H or methyl and $Y^5$ is mono-N- or di-N,N—$(C_1-C_6)$alkylamino, morpholino, piperidin-1-yl or pyrrolidin-1-yl.

The disclosure provides, at least in part, compounds represented by formula I, as depicted below. Also contemplated herein are compositions that include a compound represented by formula I and e.g., a pharmaceutically acceptable carrier.

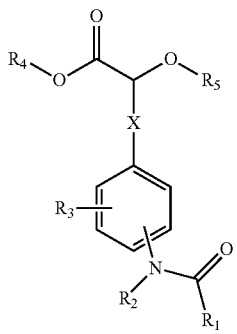

I wherein X is $C_1-C_3$alkylene, optionally substituted with one, two or three substituents selected from halogen or hydroxyl;

$R_1$ is selected from the group consisting of $C_1-C_6$alkyl, $C_3-C_6$cycloalkyl, $C_2-C_6$alkenyl, and $C_2-C_6$alkynyl;

$R_2$ is selected from the group consisting of hydrogen and $C_1-C_6$alkyl;

$R_3$ is independently selected, for each occurrence from the group consisting of hydrogen, $C_1-C_6$alkoxy, $C_1-C_6$alkyl, cyano, $C_3-C_6$cycloalkyl, halogen, hydroxyl, and nitro;

$R_4$ is selected from the group consisting of hydrogen and $C_1-C_6$alkyl;

$R_5$ is $C_1-C_6$alkyl;

or pharmaceutically acceptable salts or N-oxides thereof.

In one embodiment, $R_1$ can be $C_1-C_6$alkyl, such as methyl. In one embodiment, $R_2$ can be hydrogen. In another embodiment, $R_3$ can be selected from the group consisting of hydrogen, $C_1-C_6$alkyl, halogen, and hydroxyl. In a further embodiment, $R_3$ can be hydrogen. In one embodiment, $R_4$ and $R_5$ can each be $C_1-C_6$alkyl. In another embodiment, $R_4$ may be hydrogen and $R_5$ may be methyl. In one embodiment, X may be $(CH_2)_n$, wherein n is 1 or 2, such as 1.

In another embodiment, —$NR_2$—$COR_1$ can be in the meta position relative to X as shown in formula III.

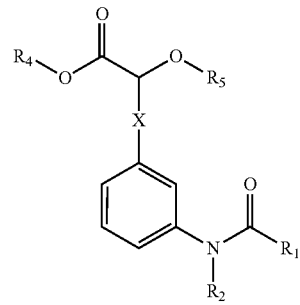

III

In another embodiment, —$NR_2$—$COR_1$ can be in the para position relative to X as shown in formula IV.

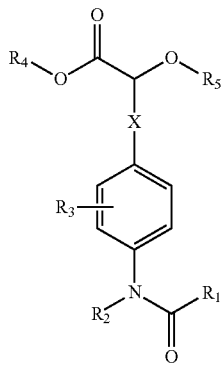

IV

The disclosure provides, at least in part, compounds represented by formula II, as depicted below. Also contemplated herein are compositions that include a compound represented by formula II and e.g., a pharmaceutically acceptable carrier.

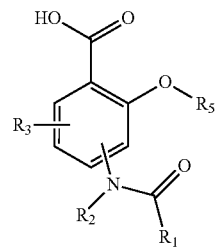

II wherein $R_1$ is selected from the group consisting of $C_1-C_6$alkyl, $C_3-C_6$cycloalkyl, $C_2-C_6$alkenyl, and $C_2-C_6$alkynyl;

$R_2$ is selected from the group consisting of hydrogen and $C_1-C_6$alkyl;

$R_3$ is independently selected, for each occurrence from the group consisting of hydrogen, $C_1-C_6$alkoxy, $C_1-C_6$alkyl, cyano, $C_3-C_6$cycloalkyl, halogen, hydroxyl, and nitro;

$R_5$ is hydrogen or $C_1-C_6$alkyl;

or pharmaceutically acceptable salts or N-oxides thereof.

Compounds of Formula V are also contemplated as shown below, as well as compositions that include a compound represented by formula V and e.g., a pharmaceutically acceptable carrier.

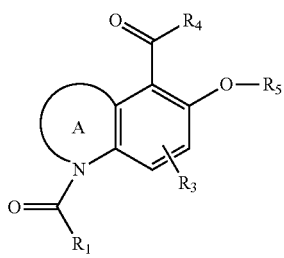

V wherein R₁ is selected from the group consisting of C₁-C₆alkyl, C₃-C₆cycloalkyl, C₂-C₆alkenyl, and C₂-C₆alkynyl;

R₃ is independently selected, for each occurrence from the group consisting of hydrogen, C₁-C₆alkoxy, cyano, C₃-C₆cycloalkyl, halogen, hydroxyl, and nitro;

R₄ is selected from the group consisting of hydrogen and C₁-C₆alkyl;

R₅ is hydrogen or C₁-C₆alkyl; and

A is a fused live or six membered heterocycle;

or pharmaceutically acceptable salts or N-oxides thereof.

In one embodiment, R₁ can be C₁-C₆alkyl, such as methyl. In another embodiment, R₁ and R₃ can each be C₁-C₆alkyl, such as methyl. In one embodiment, R₂ can be hydrogen.

In some embodiments, a compound can be represented by

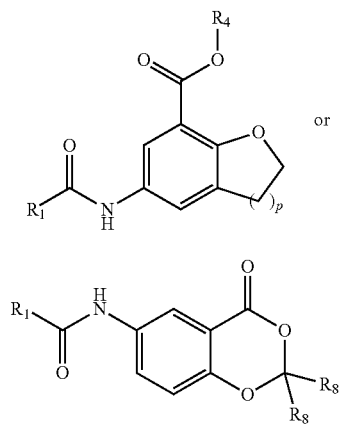

VI or

VII wherein p is 1 or 2;

R₁ is selected from the group consisting of C₁-C₆alkyl, C₃-C₆cycloalkyl, C₂-C₆alkenyl, and C₂-C₆alkynyl;

R₄ and R₈ are each independently selected from the group consisting of hydrogen and C₁-C₆alkyl;

or pharmaceutically acceptable salts or N-oxides thereof.

Contemplated compounds, and pharmaceutical compositions, comprising at least one compound, may be selected from the group consisting of: N-acetyl-(R)-3-(4-aminophenyl)-2-methoxypropionic acid (Compound A), N-acetyl-(S)-3-(4-aminophenyl)-2-methoxypropionic acid (Compound B), racemic N-acetyl-3-(4-aminophenyl)-2-methoxypropionic acid (compound AB);

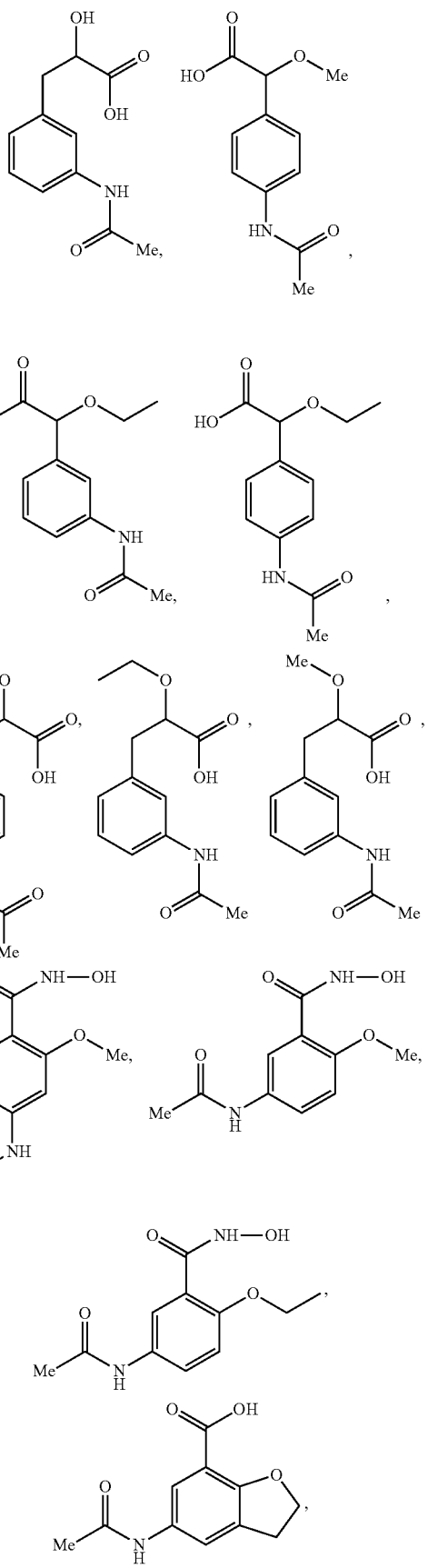

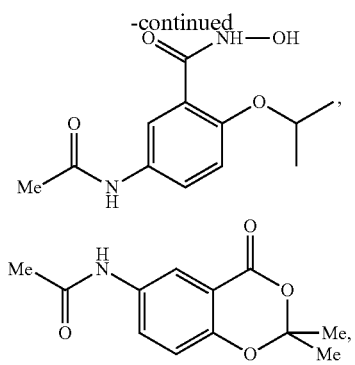

4-acetamino-N-hydroxy-2-methoxybenzamide; 1-acetyl-6-methoxy-1,2,3,4-tetrahydroquinoline-5-carboxylic acid, 5-acetamido-2hydroxybenzoic acid (e.g., acetalyated 5-aminosalicyclic acid) or pharmaceutically acceptable salts or N-oxides thereof.

The present disclosure also provides pharmaceutical compositions comprising compounds as disclosed herein formulated together with one or more pharmaceutically acceptable carriers. These formulations include those suitable for oral, rectal, topical, buccal and parenteral (e.g., subcutaneous, intramuscular, intradermal, or intravenous) administration, although the most suitable form of administration in any given case will depend on the degree and severity of the condition being treated and on the nature of the particular compound being used.

Therapeutic Applications

The disclosure further provides, in some embodiments, methods of modulating activity of one or more PPAR and/or EGF receptors comprising exposing said receptor to a compound of the invention. For example, provided herein are methods of treating a disease associated with expression or activity of one or more PPAR and/or EGF receptors in a patient comprising administering to the patient a therapeutically effective amount of a compound of the invention.

One embodiment of the invention provides a method of treating tumors of the esophagus, stomach, pancreas, colon, prostate, breast, uterus, kidneys, and lungs comprising administering to a subject in need thereof a therapeutically effective amount of a compound of the invention. Also contemplated herein is a method for delaying clinical manifestation of a colorectal tumor, or a solid tumor (e.g., a breast, prostate, lung or hepatocellular carcinoma) in a patient, for example, a patient at risk of colorectal cancer, comprising administering to the patient an effective amount of a compound disclosed herein. Administering such a compound may be on e.g., at least a daily basis. For example, the delay of clinical manifestation of a colorectal tumor in a patient as a consequence of administering a compound disclosed here may be at least e.g., 6 months, 1 year, 18 months or even 2 years or more as compared to a patient who is not administered a compound such as one disclosed herein.

Another embodiment of the invention provides a method of treating or ameliorating chronic inflammation, such as Crohn's disease or ulcerative colitis, comprising administering to a subject in need thereof a therapeutically effective amount of a compound of the invention.

Methods of treating dermatological conditions are also provided, such as the treatment of at least one of: acne vulgaris, comedo-type acne, polymorphic acne, acne rosacea, nodulocystic acne, acne conglobata, senile acne, secondary acne, solar acne, acne medicamentosa or occupational acne, ichthyosis, Darrier's disease, keratosis palmaris or plantaris, cutaneous, mucosal or ungual psoriasis, skin disorders due to exposure to UV radiation, of skin aging, photoinduced or chronological or actinic pigmentations and keratoses, acne hyperseborrhoea, simple seborrhoea or seborrhoeic cicatrization disorders or stretch marks. Methods of treating atopic dermatitis is also contemplated. The composition may be administered orally or topically.

For example, continuous sebum production can increase in acne patients; and application of a sebum inhibitor, such as disclosed herein, may be useful in the treatment of acne, seborrhea or alopecia. In another example, chronic inflammation of hair follicles (keratinocytes) can be an indication of e.g., androgenic alopecia. An inhibitor of such inflammation such as disclosed herein can be useful in e.g., the treatment of hair loss.

Provided herein are methods of treating fine lines, wrinkles or surface irregularities of the skin, or protecting from and/or ameliorating free radical damage to the skin, comprising topically administering an effective amount of a composition comprising a compound of the invention.

In some embodiments, a method of treating hair loss in a patient suffering from unwanted hair loss is provided, comprising administering an effective amount of a composition comprising a disclosed compound. Methods of treating alopecia areata, androgenetic alopecia and/or telogenic defluvium we contemplated.

Also provided herein are methods of treating an age-related disorder selected from the group consisting of: diabetes, cataracts, Alzheimer's disease, Parkinson's disease, macular degeneration, retinal ulcers or retinal vasculitis, comprising administering an effective amount of a composition comprising a disclosed compound. Also provided herein are methods of treating a vascular or cardiac disorder, comprising identifying a patient suffering from or at risk of developing said disorder and administering to said patient an effective amount of a disclosed compound as defined above. For example, a cardiac disorder being treated may be chosen from chronic coronary ischemia, arteriosclerosis, congestive heart failure, ischemic or reperfusion related injury, angina, atherosclerosis, myocardial infarction, stroke and myocardial hypertrophy. In another embodiment, a method of treating an autoimmune disorder is provided, wherein the autoimmune disorder may be chosen from, for example, Addison's disease, chronic thyroiditis, dermatomyositis, Grave's disease, multiple sclerosis, systemic lupus erythematosis, psoriasis, or rheumatoid arthritis. (Intra-articular administration of disclosed compounds and/or compositions is contemplated herein, in some embodiments, for e.g., arthritis or any other contemplated indication). Other contemplated indications include mucosal disorders such as aphtae (mouth ulcers) and/or gingivitis. In another embodiment, treatment of ocular disorders is also contemplated such as diabetic retinopathy or age-related macular degeneration.

The compounds of the invention may be administered to patients (animals and humans) in need of such treatment in dosages that will provide optimal pharmaceutical efficacy. It will be appreciated that the dose required for use in any particular application will vary from patient to patient, not only with the particular compound or composition selected, but also with the route of administration, the nature of the condition being treated, the age and condition of the patient, concurrent medication or special diets then being followed by the patient, and other factors which those skilled in the art will recognize, with the appropriate dosage ultimately being at the discretion of the attendant physician. For treating clinical conditions and diseases noted above, the compound of this invention may be administered orally, topically, parenterally, by inhalation spray or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques.

Generally, a therapeutically effective amount of active component will be in the range of from about 0.1 mg/kg to about 100 mg/kg, optionally from about 1 mg/kg to about 100 mg/kg, optionally from about 1 mg/kg to 10 mg/kg. The amount administered will depend on variables such as the type and extent of disease or indication to be treated, the overall health status of the particular patient, the relative biological efficacy of the compounds, formulation of compounds, the presence and types of excipients in the formulation, and the route of administration. The initial dosage administered may be increased beyond the upper level in order to rapidly achieve the desired blood-level or tissue level, or the initial dosage may be smaller than the optimum and the daily dosage may be progressively increased during the course of treatment depending on the particular situation. Human dosage can be optimized, e.g., in a conventional Phase I dose escalation study designed to run from 0.5 mg/kg to 20 mg/kg. Dosing frequency can vary, depending on factors such as route of administration, dosage amount and the disease condition being treated. Exemplary dosing frequencies are once per day, once per week and once every two weeks.

Contemplated formulations or compositions comprise a disclosed compound and typically include a compound a pharmaceutically acceptable carrier.

Contemplated compositions may be administered by various means, depending on their intended use, as is well known in the art. For example, if compositions of the present invention are to be administered orally, they may be formulated as tablets, capsules, granules, powders or syrups. Alternatively, formulations of the present invention may be administered parenterally as injections (intravenous, intramuscular or subcutaneous), drop infusion preparations or enemas or suppositories. For application by the ophthalmic mucous membrane route, compositions of the present invention may be formulated as eyedrops or eye ointments. These formulations may be prepared by conventional means, and, if desired, the compositions may be mixed with any conventional additive, such as an excipient, a binder, a disintegrating agent, a lubricant, a corrigent, a solubilizing agent, a suspension aid, an emulsifying agent or a coating agent.

In formulations of the subject invention, wetting agents, emulsifiers and lubricants, such as sodium lauryl sulfate and magnesium stearate, as well as coloring agents, release agents, coating agents, sweetening, flavoring and perfuming agents, preservatives and antioxidants may be present in the formulated agents.

Subject compositions may be suitable for oral, nasal, topical (including buccal and sublingual), rectal, vaginal, aerosol and/or parenteral administration. The formulations may conveniently be presented in unit dosage form and may be prepared by any methods well known in the art of pharmacy. The amount of composition that may be combined with a carrier material to produce a single dose vary depending upon the subject being treated, and the particular mode of administration.

Methods of preparing these formulations include the step of bringing into association compositions of the present invention with the carrier and, optionally, one or more accessory ingredients. In general, the formulations are prepared by uniformly and intimately bringing into association agents with liquid carriers, or finely divided solid carriers, or both, and then, if necessary, shaping the product.

Formulations suitable for oral administration may be in the form of capsules, cachets, pills, tablets, lozenges (using a flavored basis, usually sucrose and acacia or tragacanth), powders, granules, or as a solution or a suspension in an aqueous or non-aqueous liquid, or as an oil-in-water or water-in-oil liquid emulsion, or as an elixir or syrup, or as pastilles (using an inert base, such as gelatin and glycerin, or sucrose and acacia), each containing a predetermined amount of a subject composition thereof as an active ingredient. Compositions of the present invention may also be administered as a bolus, electuary, or paste.

In solid dosage forms for oral administration (capsules, tablets, pills, film-coated tablets, sugar-coated tablets, powders, granules and the like), the subject composition is mixed with one or more pharmaceutically acceptable carriers, such as sodium citrate or dicalcium phosphate, and/or any of the following: (1) fillers or extenders, such as starches, lactose, sucrose, glucose, mannitol, and/or silicic acid; (2) binders, such as, for example, carboxymethylcellulose, alginates, gelatin, polyvinyl pyrrolidone, sucrose and/or acacia; (3) humectants, such as glycerol; (4) disintegrating agents, such as agar-agar, calcium carbonate, potato or tapioca starch, alginic acid, certain silicates, and sodium carbonate; (5) solution retarding agents, such as paraffin; (6) absorption accelerators, such as quaternary ammonium compounds; (7) wetting agents, such as, for example, acetyl alcohol and glycerol monostearate; (8) absorbents, such as kaolin and bentonite clay; (9) lubricants, such a talc, calcium stearate, magnesium stearate, solid polyethylene glycols, sodium lauryl sulfate, and mixtures thereof; and (10) coloring agents. In the case of capsules, tablets and pills, the compositions may also comprise buffering agents. Solid compositions of a similar type may also be employed as fillers in soft and hard-filled gelatin capsules using such excipients as lactose or milk sugars, as well as high molecular weight polyethylene glycols and the like.

Formulations and compositions may include micronized crystals of the disclosed compounds. Micronization may be performed on crystals of the compounds alone, or on a mixture of crystals and a part or whole of pharmaceutical excipients or carriers. Mean particle size of micronized crystals of a disclosed compound may be for example about 5 to about 200 microns, or about 10 to about 110 microns.

A tablet may be made by compression or molding, optionally with one or more accessory ingredients. Compressed tablets may be prepared using binder (for example, gelatin or hydroxypropylmethyl cellulose), lubricant, inert diluent, preservative, disintegrant (for example, sodium starch glycolate or cross-linked sodium carboxymethyl cellulose), surface-active or dispersing agent. Molded tablets may be made by molding in a suitable machine a mixture of the subject composition moistened with an inert liquid diluent. Tablets, and other solid dosage forms, such as film coated tablets or sugar coated tablets, capsules, pills and granules, may optionally be scored or prepared with coatings and shells, such as enteric coatings and other coatings well known in the pharmaceutical-formulating art.

Liquid dosage forms for oral administration include pharmaceutically acceptable emulsions, microemulsions, solutions, suspensions, syrups and elixirs. In addition to the subject composition, the liquid dosage forms may contain inert diluents commonly used in the art, such as, for example, water or other solvents, solubilizing agents and emulsifiers, such as ethyl alcohol, isopropyl alcohol, ethyl carbonate, ethyl acetate, benzyl alcohol, benzyl benzoate, propylene glycol, 1,3-butylene glycol, oils (in particular, cottonseed, groundnut, corn, germ, olive, castor and sesame oils), glycerol, tetrahydrofuryl alcohol, polyethylene glycols and fatty acid esters of sorbitan, cyclodextrins and mixtures thereof.

Suspensions, in addition to the subject composition, may contain suspending agents as, for example, ethoxylated isostearyl alcohols, polyoxyethylene sorbitol and sorbitan esters, microcrystalline cellulose, aluminum metahydroxide, bentonite, agar-agar and tragacanth, and mixtures thereof.

Formulations for rectal or vaginal administration may be presented as a suppository, which may be prepared by mixing a subject composition with one or more suitable non-irritating excipients or carriers comprising, for example, cocoa butter, polyethylene glycol, a suppository wax or a salicylate, and which is solid at room temperature, but liquid at body temperature and, therefore, will melt in the body cavity and release the active agent. Formulations which are suitable for vaginal administration also include pessaries, tampons, creams, gels, pastes, foams or spray formulations containing such carriers as are known in the art to be appropriate.

Dosage forms for transdermal or topical administration of a subject composition include powders, sprays, ointments, pastes, creams, lotions, gels, solutions, patches and inhalants. The active component may be mixed under sterile conditions with a pharmaceutically acceptable carrier, and with any preservatives, buffers, or propellants which may be required.

The ointments, pastes, creams and gels may contain, in addition to a subject composition, excipients, such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays may contain, in addition to a subject composition, excipients such as lactose, talc, silicic acid, aluminum hydroxide, calcium silicates and polyamide powder, or mixtures of these substances. Sprays may additionally contain customary propellants, such as chlorofluorohydrocarbons and volatile unsubstituted hydrocarbons, such as butane and propane.

Compositions and compounds of the present invention may alternatively be administered by aerosol. This is accomplished by preparing an aqueous aerosol, liposomal preparation or solid particles containing the compound. A non-aqueous (e.g., fluorocarbon propellant) suspension could be used. Sonic nebulizers may be used because they minimize exposing the agent to shear, which may result in degradation of the compounds contained in the subject compositions.

Ordinarily, an aqueous aerosol is made by formulating an aqueous solution or suspension of a subject composition together with conventional pharmaceutically acceptable carriers and stabilizers. The carriers and stabilizers vary with the requirements of the particular subject composition, but typically include non-ionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Pharmaceutical compositions of this invention suitable for parenteral administration comprise a subject composition in combination with one or more pharmaceutically-acceptable sterile isotonic aqueous or non-aqueous solutions, dispersions, suspensions or emulsions, or sterile powders which may be reconstituted into sterile injectable solutions or dispersions just prior to use, which may contain antioxidants, buffers, bacteriostats, solutes which render the formulation isotonic with the blood of the intended recipient or suspending or thickening agents.

Examples of suitable aqueous and non-aqueous carriers which may be employed in the pharmaceutical compositions of the invention include water, ethanol, polyols (such as glycerol, propylene glycol, polyethylene glycol, and the like), and suitable mixtures thereof, vegetable oils, such as olive oil, and injectable organic esters, such as ethyl oleate and cyclodextrins. Proper fluidity may be maintained, for example, by the use of coating materials, such as lecithin, by the maintenance of the required particle size in the case of dispersions, and by the use of surfactants. The efficacy of treatment with the subject compositions may be determined in a number of fashions known to those of skill in the art.

Throughout the description, where compositions are described as having, including, or comprising specific components, it is contemplated that compositions also consist essentially of, or consist of, the recited components. Similarly, where processes are described as having, including, or comprising specific process steps, the processes also consist essentially of, or consist of, the recited processing steps. Except where indicated otherwise, the order of steps or order for performing certain actions are immaterial so long as the invention remains operable. Moreover, unless otherwise noted, two or more steps or actions may be conducted simultaneously.

EXAMPLES

The compounds of the present invention can be prepared in a number of ways well known to one skilled in the art of organic synthesis. More specifically, compounds of the invention may be prepared using the reactions and techniques described herein. In the description of the synthetic methods described below, it is to be understood that all proposed reaction conditions, including choice of solvent, reaction atmosphere, reaction temperature, duration of the experiment and workup procedures, can be chosen to be the coed standard for that reaction, unless otherwise indicated. It is understood by one skilled in the art of organic synthesis that the functionality present on various portions of the molecule should be compatible with the reagents and reactions proposed. Substituents not compatible with the reaction conditions will be apparent to one skilled in the art, and alternate methods are therefore indicated. The starting materials for the examples are either commercially available or are readily prepared by standard methods from known materials.

Example 1

Preparation of N-acetyl-(R)-(−)-3-(4-aminophenyl)-2-methoxypropionic acid (N-Acetyl E2); Compound A To (R)-(−)-3-(4-aminophenyl)-2-methoxypropionic acid (40 g) in a 0.5 L glass reactor was added ethyl acetate (80 g) and acetic anhydride (62.8 g). The mixture was stirred at 90° C. for 1 hour. Upon cooling, the solvent was removed by vacuum distillation, providing an oily residue. To this residue was added water (120 g) and ethyl acetate (120 g). After stirring for 10 min at 35° C., the layers were separated and the aqueous layer discarded. The organic layer solvent was removed by vacuum distillation. Acetone (120 g) was then added and the resulting mixture was warmed until dissolution was complete. The solution was cooled to 0° C., and the product precipitated which was collected by filtration. The solid was rinsed with acetone (20 g) and dried at 65° C. to afford 26 g of the title compound.

Example 2

Docking Studies

The binding of compounds A, B, and their non-acetylated derivatives, (as well as 5-aminosalicyclic acid (5-ASA) and 5-acetamido-hydroxybenzoic acid) to PPARγ and PPARα receptors is evaluated.

While 5-ASA shows good affinity for PPARγ, the N-acetylation of 5-ASA led to a rigid linear structure that did not occupy the active site in a optimal way. A loss of the hydrogen bond between H449 and the phenolic group oldie compound occurred which may explain the inactivity of NAc-5-ASA. The binding of compound B and its non-acetylated counterpart into PPARγ indicated that these compounds may activate the receptor based on the receptor's binding structural prerequisites. Superposition of the compounds indicated that they bind to different parts of the active site.

The binding of compound A and its non acetylated counterpart 3-(4-aminophenyl)-2-methoxypropanoic acid) into PPARγ indicated that these compounds may also activate the receptor. In contrast to compound B, the superposition compound A free amine and N-acetyl derivative show that they occupy the same portion of the active site, indicating a possible similarity in activity.

Example 3

Anti-Murine Colitis Model

Colitis in C57bI6 mice is induced by administering TNBS (150 mg/kg) by oral gavage on day −3. Stool samples were taken 8 hours after administration. At day 0-5, N-acetylated E2 (30 mM) was administered by oral gavage. On day 5, mice were analyzed to obtain a mortality macroscopic score (Wallace, *Gastroenterology* 96: 29-36, 1989).

Figure 2:
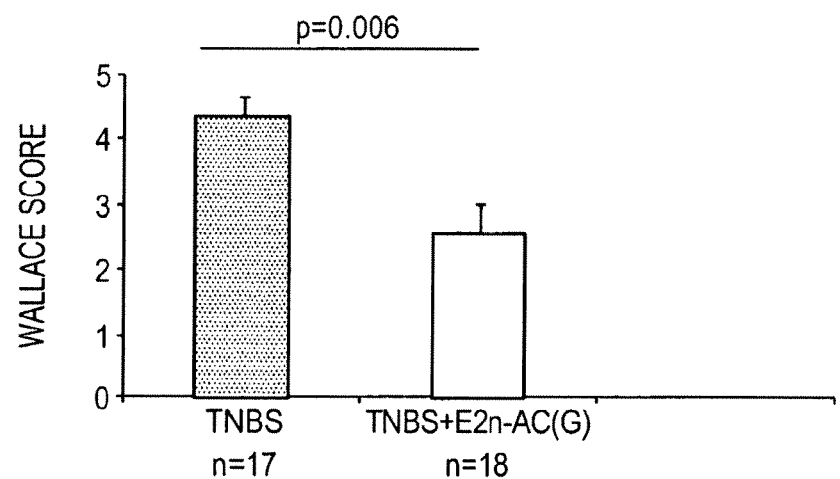
FIG. 2 depicts the observed level of colonic lesions in mice receiving TNBS versus mice receiving TNBS and N-acetyl E2 in a murine colitis model.
Figure 3:
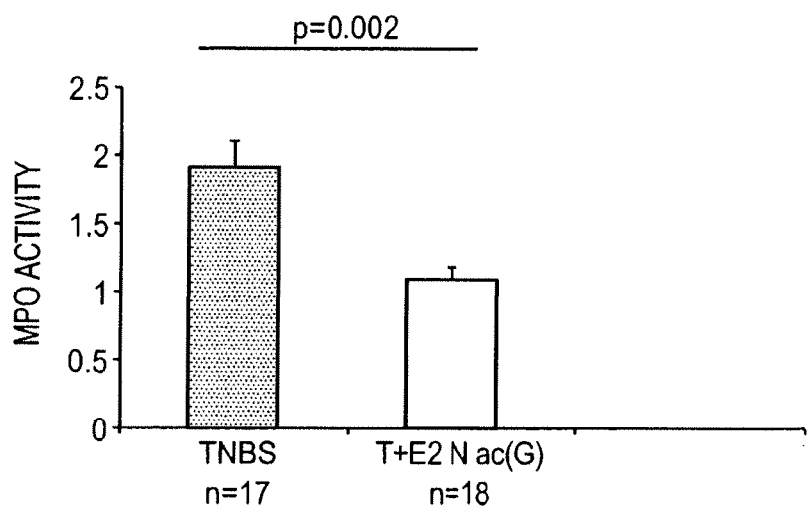
FIG. 3 depicts the observed level of MPO activity in mice receiving TNBS versus mice receiving TNBS and N-acetyl E2 in a murine colitis model.
Figure 4:
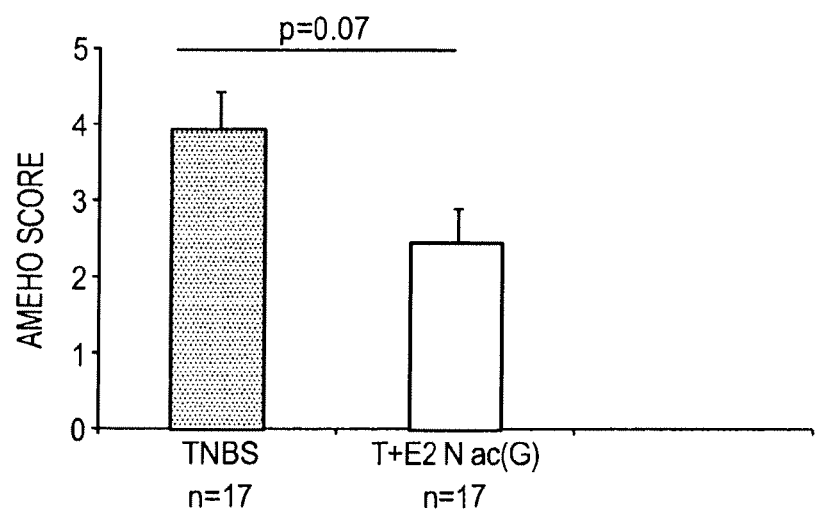
FIG. 4 depicts the observed level of colonic inflammation in mice receiving TNBS versus mice receiving TNBS and N-acetyl E2 in a murine colitis model.

As shown in FIG. 1, mortality was comparable between mice given TNBS versus those given TNBS and N-acetyl E2. However, as shown in FIG. 2, the level of colonic lesions was significantly less in mice given TNBS and N-acetyl E2 compared to those given TNBS alone. FIG. 3 demonstrates how MPO (myleoperoxidase) decreased with administration of N-acetyl E2 with TNBS. In FIG. 4, the Ameho score (*Gut* 41: 487-493, 1997) indicated that colonic inflammation had decreased with administration of N-acetyl E2 with TNBS.

Example 4

Keratinocytes

Figure 5:
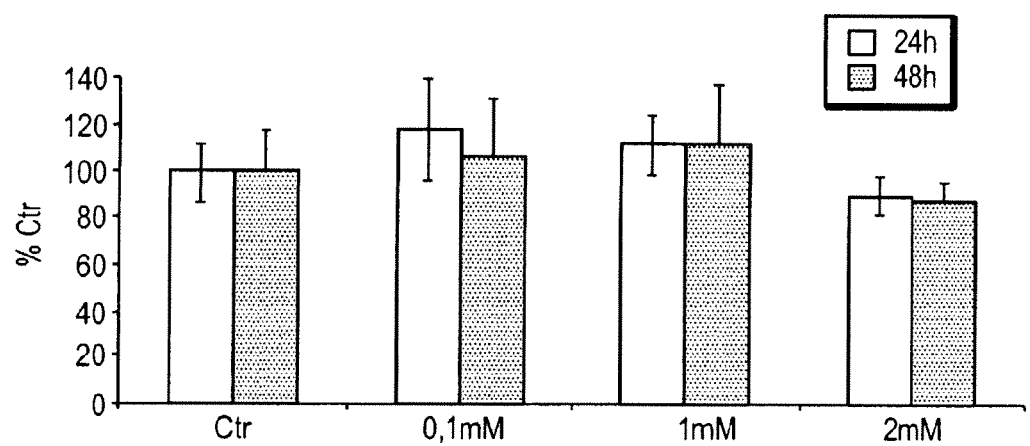
FIG. 5 depicts effects ail disclosed compound on human keratinocytes.

To assess the possible toxic or cytostatic effect of the substances under study, a spectrophotometric test (MTT) was carried out. The human primary keratinocytes, isolated from skin biopsies, were plated in wells of a 24-well plate in suitable medium with addition of antibiotics, calcium, and specific growth factors. At around 70% confluence, the cells were exposed to the presence of Compound A, at various concentrations (0.1-1-2 mM), for 24 and 48 h in suitable medium with addition of antibiotics, calcium, but no growth factors. This culture condition was done for all the subsequent experiments. At the end of the treatment, the MTT test was done. The results are indicated in FIG. 5. Compound A in all concentrations used did not show any effect on cellular vitality.

Example 5

TNF Alpha

Figure 6:
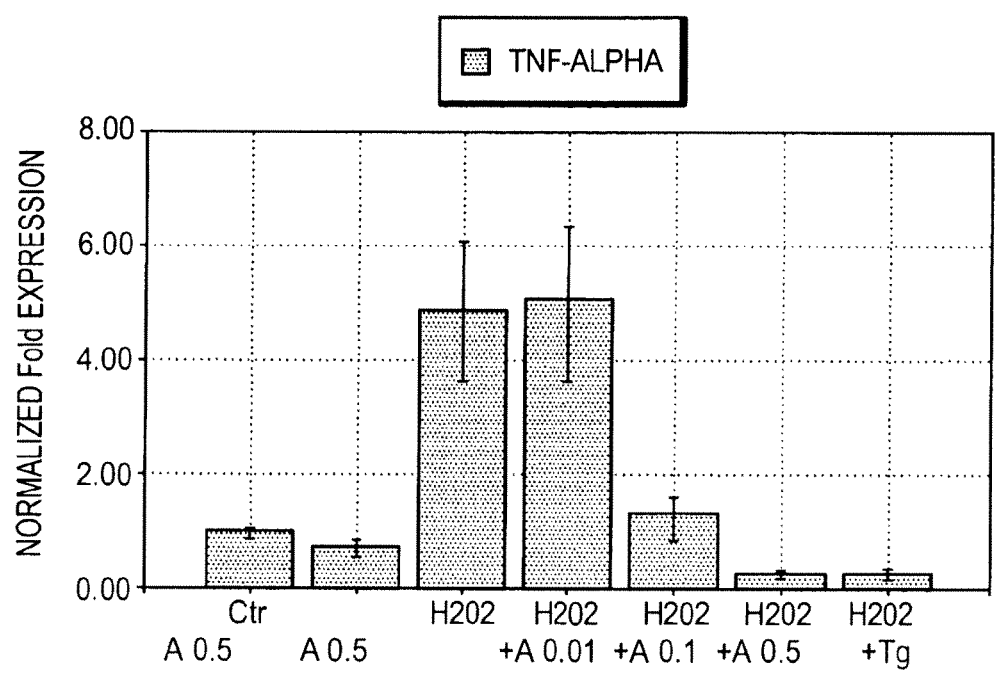
FIG. 6 depicts inhibition of TNF alpha by $H_2O_2$ and a disclosed compound.

Analysis of the inhibition of compound A of the mRNA induction of the proinflammatory cytokine TNF-alpha by $H_2O_2$ was carried out by Real time RT-PCR. The keratinocytes were plated in dishes of 6 cm/Ø. At 80% confluence, the cells were treated with $H_2O_2$ (300 µM) in presence of Compound A at the three concentrations (0.01-0.1-0.5 mM) for 6 h. At the end of the treatment, the cells were lysed in a lysis buffer and subjected to isolation and subsequent retrotranscription of the RNA. Compound A proved able to inhibit the expression of the mRNA of TNF-α induced by $H_2O_2$ at the two higher doses (0.1 mM; 0.5 mM). The higher dose demonstrated a complete inhibition of the proinflammatory cytokine with an effect similar to troglitazone (Tg). (FIG. 6)

Example 6

Inhibition of mRNA Expression IL-6 Induced by Presence of IFN-γ

Analysis of the inhibition by compound A of the mRNA induction of the proinflammatory cytokine IL-6 by IFN-γ was done through Real time RT-PCR. The keratinocytes were plated in dishes of 6 cm/Ø.

Figure 7:
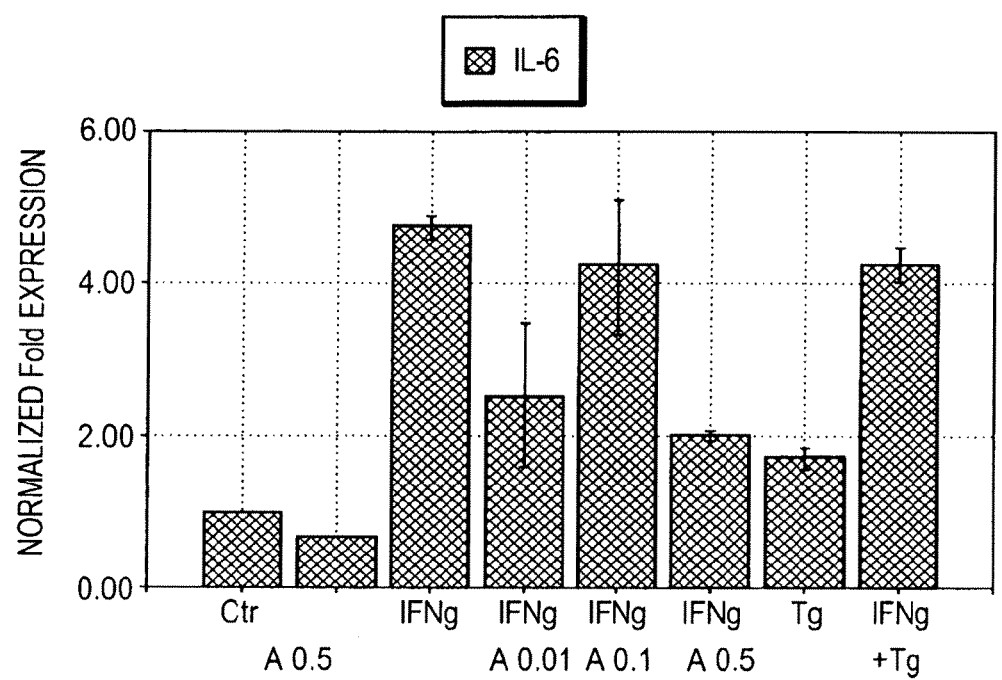
FIG. 7 depicts inhibition on mRNA expression of IL-6 induced by the presence of IFN-gamma.

At 80% confluence, the cells were treated with IFN-γ (30 ng/ml) in presence of compound A (N-Acetylged) at the three concentrations (0.01-0.1-0.5 mM) for 6 h. At the end of the treatment, the cells were lysed in a lysis buffer and subjected to isolation and subsequent retrotranscription of the RNA The results (as shown in FIG. 7) reveal the ability of Compound A to inhibit the expression of the inflammatory cytokine induced by presence of IFN-γ which does not appear to be dose-dependent.

Example 7

Inhibitory Capacity on the Activation of Nuclear Factor NF-kB Induced by Presence of $H_2O_2$ Evaluation of the inhibition by compound A of the activation of nuclear transcription factor NF-kB induced by the presence of $H_2O_2$ was done by analysis in cytofluorimetry.

Figure 8:
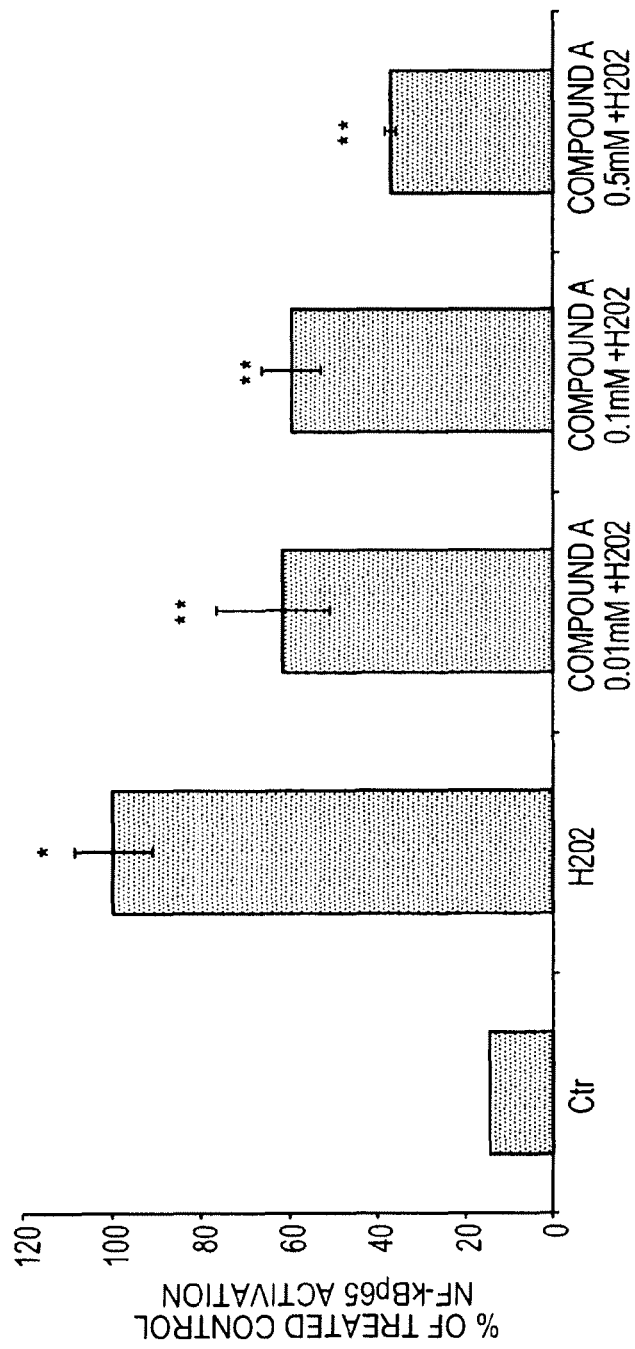
FIG. 8 depicts inhibition of a disclosed compound on the activation of NF-kB.

The keratinocytes were plated in wells of a 12-well plate. At 80% confluence, the cells were treated with $H_2O_2$ (300 µM) in presence of compound A at the three concentrations (0.01-0.1-0.5 mM) for 1 h. At the end of the treatment, the cells were fixed in paraformaldehyde, permeabilized in methanol and then incubated in presence of the specific antibody of subunit p65. Compound A revealed an inhibitory effect on the activation and subsequent translocation of NF-kB in dose-dependent manner (FIG. 8).

Example 8

Inhibition of Protein Expression of IL-6 Induced by Presence of LPS

Figure 9:
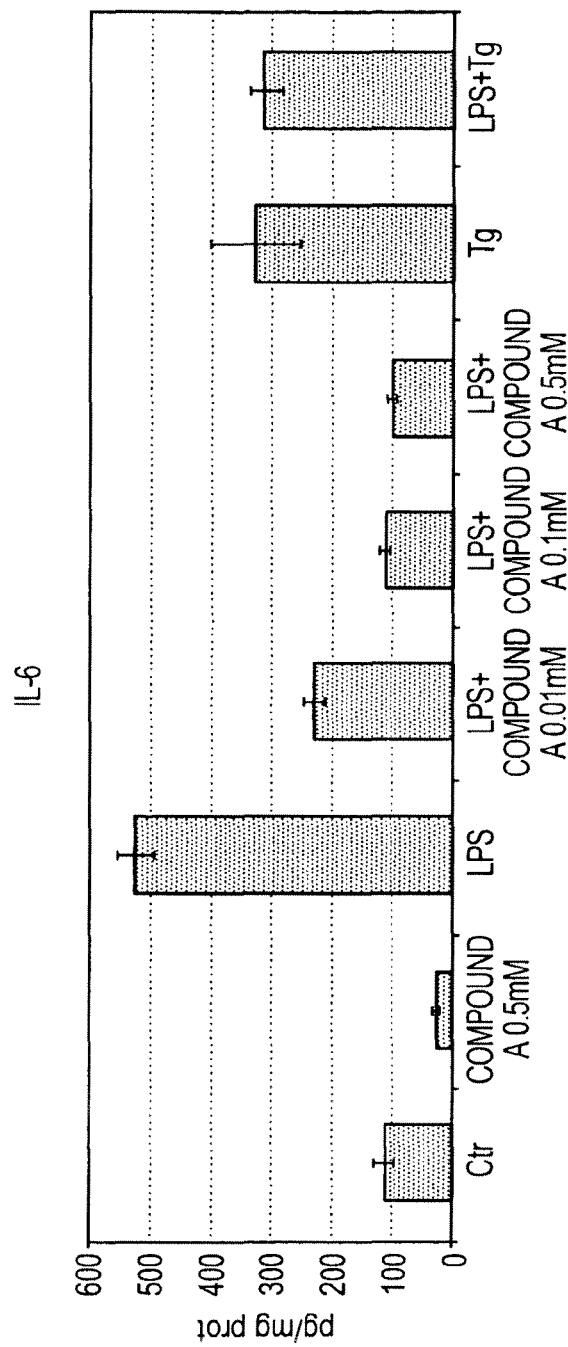
FIG. 9 depicts inhibition of a disclosed compound on protein expression of IL-6 induced by presence of LPS.

Analysis of the inhibition by Compound A of the protein induction of IL-6 by LPS (lipopolysaccharide) was done with the ELISA kit. The keratinocytes were plated in wells of a 24-well plate. At 80% confluence, the cells were treated with LPS (10 μg/ml) in presence of compound A at the three concentrations (0.01-0.1-0.5 mM) for 24 h. At the end of the treatment, the supernatant was decanted, centrifuged so as to remove any cell detritus, and kept at −80° C. until the time of the analysis. The quantity of IL-6 present in the supernatant was normalized by the protein concentration of the sample itself. The results (FIG. 9) revealed the ability of compound A to inhibit, in dose-dependent manner, the protein expression of the inflammatory cytokine under study.

Example 9

Human Sebocytes

Figure 10:
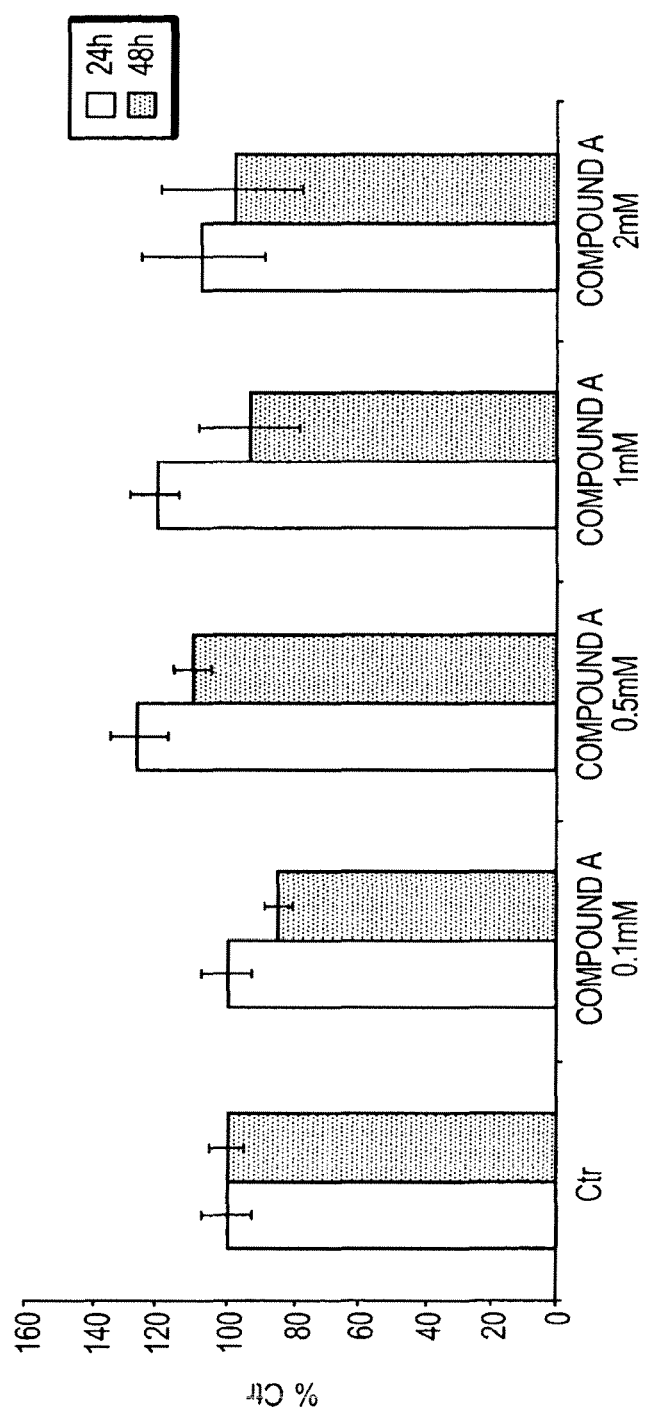
FIG. 10 depicts effect of a disclosed compound on human sebocytes.

To assess the possible toxic or cytostatic effect of the substances under study, a spectrophotometric test (MTT) was carried out. The sebocytes were plated in wells of a 24-well plate in suitable medium with addition of antibiotics, calcium and EGF. At roughly 70% confluence, the cells were exposed to the presence of compound A, in various concentrations (0.1-0.5-1-2 mM), for 24 and 48 h. At the end of the treatment, the MTT test was performed. Compound A in all concentrations used demonstrated no effects on cell vitality. (FIG. 10)

Example 10

Evaluation of the Inhibitory Capacity of a Compound on Sebogenesis Induced by Stimuli of Lipid Type (Linoleic Acid, Testosterone)

Figure 11:
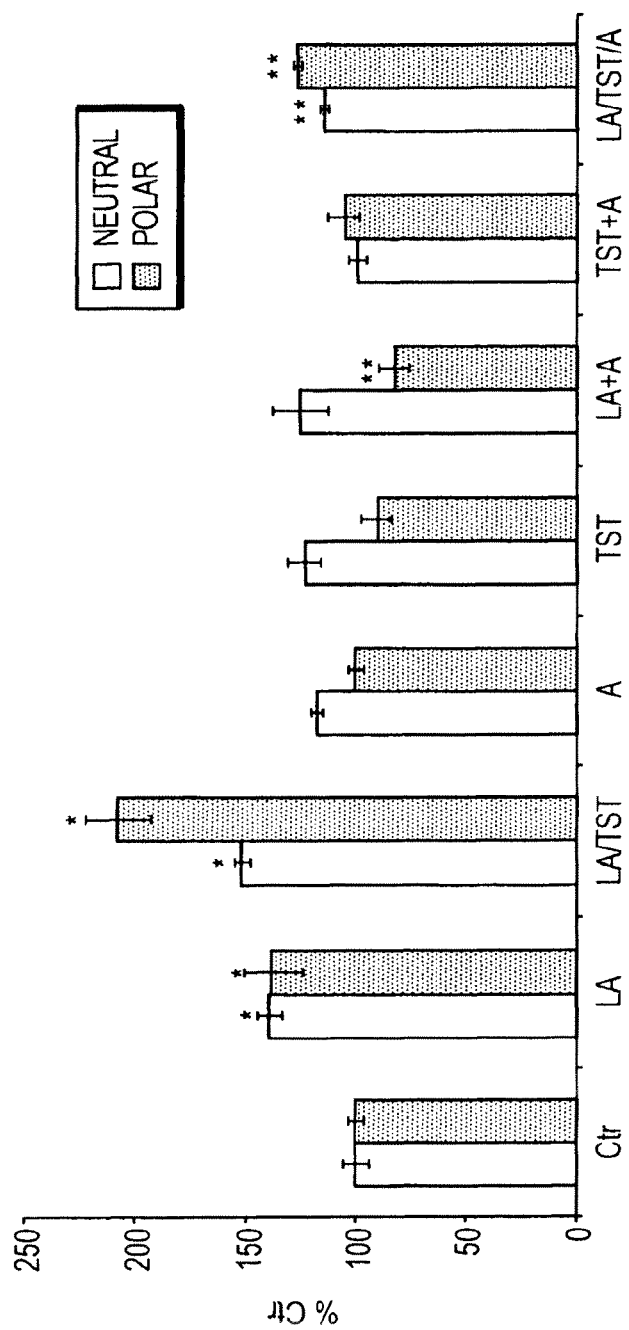
FIG. 11 depicts inhibitory capacity of a disclosed compound on sebogenesis induced by lipid type stimulus.

Analysis of the inhibition by (compound A) of sebogenesis induced by treatment with linoleic acid (LA) and with testosterone (TST) was evaluated by spectrofluorimetry, using Nile Red as selective marker of intracellular lipids (Nile Red Assay). The sebocytes were plated in wells of a 24-well plate. Next day, they were deprived of serum (2%) and after 24 h they were stimulated, for another 24 h, with LA (10-4M), TST (20 nM) in presence or in absence of A (1 mM). At the end of the treatment, the sebocytes were stained with Nile Red. The quantitative analysis was done by spectrofluorimetry, which made it possible to distinguish between neutral lipids and polar lipids based on the different wavelength of excitation and emission. The data obtained revealed that the treatment with LA is able to induce lipid synthesis and that the combined LA+TST treatment further increases this effect. The presence of Compound A proved able to reduce the lipidogenic stimulus. (FIG. 11).

Example 11

Figure 12A:
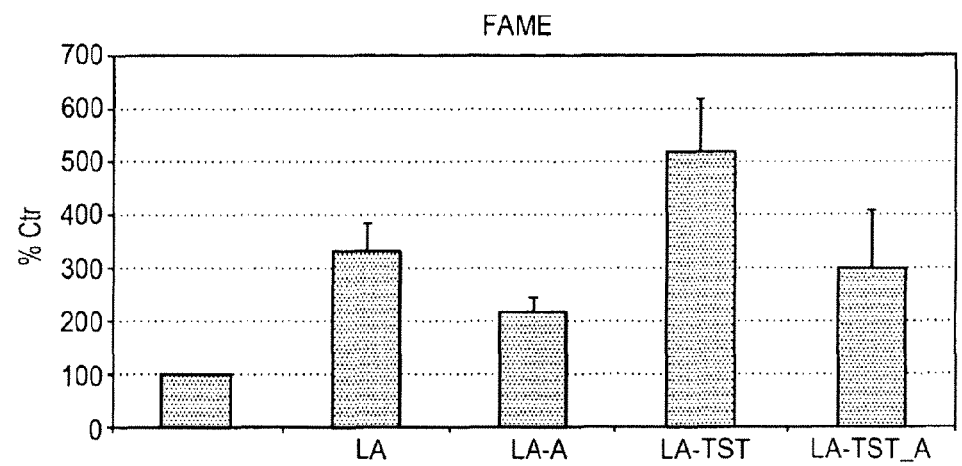
FIG. 12 depicts the results of a fatty acid assay (A) and squalene analysis (B) of sebogenesis
Figure 12B:
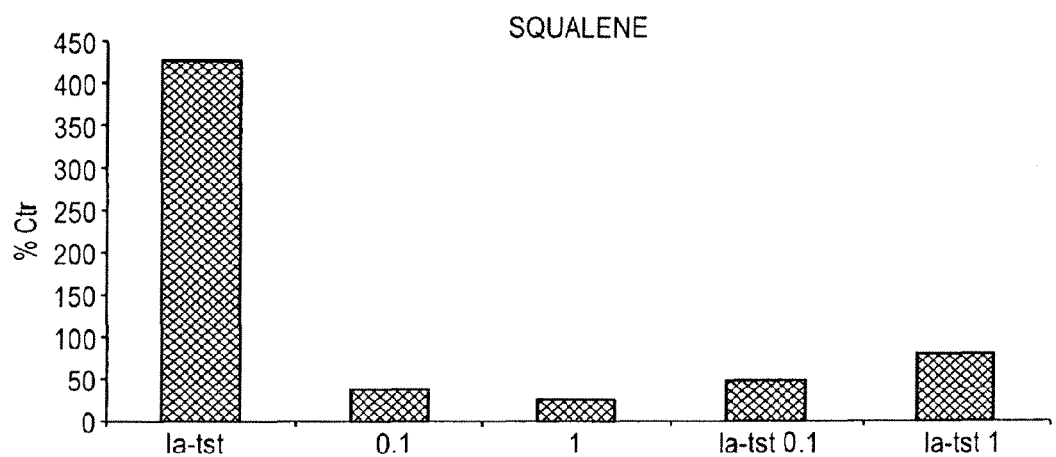

Evaluation of the Inhibitory Capacity on Sebogenesis Induced by Stimuli of Lipid Type (Linoleic Acid, Testosterone): Evaluation of Fatty Acids and Squalene In order to evaluate in greater detail the inhibition by Compound A of sebogenesis induced by LA and TST, assays were performed on the lipid extract of the sebocytes using gas chromatography coupled with mass spectrometry (GC-MS). The sebocytes were treated by the scheme described for the Nile Red assay. At the end of the treatment, the cells were removed and then the lipid extraction was done by using organic solvents. One part of the extract was used to analyze the fatty acid composition, while the other part was used for the determination of the quantity of squalene, a lipid characteristic of sebum. The fatty acid assay showed that the lipidogenic stimulus induced by the treatment with LA and LA-t-TST was reduced by the presence of A (FIG. 12A). These results are confirmed by the squalene analysis. (FIG. 12B)

Example 12

Evaluation of the Inhibitory Capacity on Sebogenesis Induced by Stimuli of Lipid Type (Linoleic Acid, Testosterone)

Figure 13:
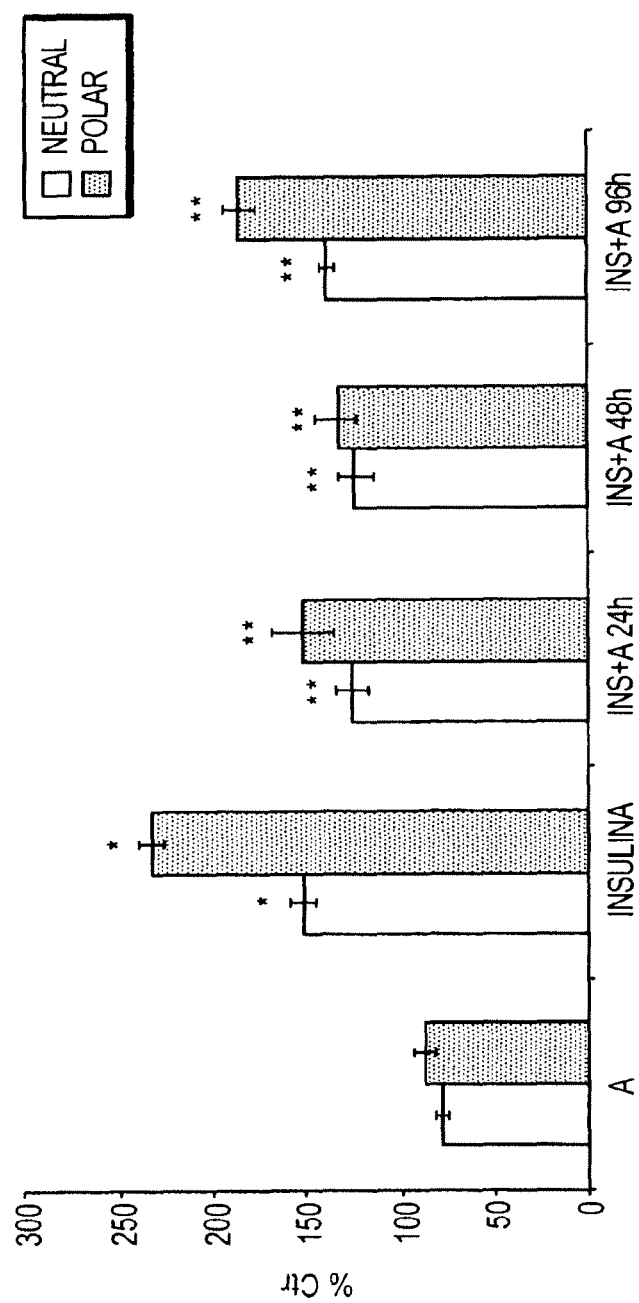
FIG. 13 depicts treatment with linoleic acid and testosterone with lipidogenic stimulus.

Analysis of the inhibition by compound A of sebogenesis induced by treatment with linoleic acid (LA) and with testosterone (TST) was evaluated by spectrofluorimetry, using Nile Red as selective marker of intracellular lipids (Nile Red Assay). The sebocytes were plated in wells of a 24-well plate. Next day, they were deprived of serum (2%) and after 24 h they were stimulated, for another 24 h, with LA (10-4M), TST (20 nM) in presence or in absence of compound A (1 mM). At the end of the treatment, the sebocytes were stained with Nile Red. The quantitative analysis was done by spectrofluorimetry, which made it possible to distinguish between neutral lipids and polar lipids based on the different wavelength of excitation and emission. The data obtained (FIG. 13) revealed that the treatment with LA is able to induce lipid synthesis and that the combined LA+TST treatment further increases this effect. The presence of A proved able to reduce the lipidogenic stimulus. No differences were observed in regard to the times of treatment with the A.

REFERENCES

All publications and patents mentioned herein, including those items listed below, are hereby incorporated by reference in their entirety as if each individual publication or patent was specifically and individually incorporated by reference. In case of conflict, the present application, including any definitions herein, will control.

EQUIVALENTS

While specific embodiments of the subject invention have been discussed, the above specification is illustrative and not restrictive. Many variations of the invention will become apparent to those skilled in the art upon review of this specification. The full scope of the invention should be determined by reference to the claims, along with their full scope of equivalents, and the specification, along with such variations.

Unless otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in this specification and attached claims are approximations that may vary depending upon the desired properties sought to be obtained by the present invention.

What is claimed is:

1. A method of treating psoriasis in a subject in need thereof, comprising administering a pharmaceutically effective amount of the compound N-acetyl-(R)-3-(4-aminophenyl)-2-methoxypropionic acid or a pharmaceutically acceptable salt or N-oxide thereof.

2. The method of claim 1, wherein the psoriasis is at least one of: cutaneous, mucosal or ungual psoriasis.

3. The method of claim 1, wherein the compound is administered orally or topically.

4. A method of treating psoriasis comprising administering a pharmaceutically effective amount of a pharmaceutical composition, wherein the pharmaceutical composition comprises:
   N-acetyl-(R)-3-(4-aminophenyl)-2-methoxypropionic acid or a pharmaceutically acceptable salt or N-oxide thereof, and
   a pharmaceutically acceptable carrier.

5. A method of treating psoriasis in a subject in need thereof, comprising administering a pharmaceutically effective amount of the compound N-acetyl-(S)-3-(4-aminophenyl)-2-methoxypropionic acid or a pharmaceutically acceptable salt or N-oxide thereof.

6. The method of claim 5, wherein the psoriasis is at least one of: cutaneous, mucosal or ungual psoriasis.

7. The method of claim 5, wherein the compound is administered orally or topically.

8. A method of treating psoriasis comprising administering a pharmaceutically effective amount of a pharmaceutical composition, wherein the pharmaceutical composition comprises:
   N-acetyl-(S)-3-(4-aminophenyl)-2-methoxypropionic acid or a pharmaceutically acceptable salt or N-oxide thereof, and
   a pharmaceutically acceptable carrier.

* * * * *